(12) United States Patent
Kiesel et al.

(10) Patent No.: US 8,263,955 B2
(45) Date of Patent: Sep. 11, 2012

(54) CAUSING RELATIVE MOTION

(75) Inventors: Peter Kiesel, Palo Alto, CA (US);
Markus Beck, Palo Alto, CA (US);
Michael Bassler, Erlangen (DE); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 854 days.

(21) Appl. No.: 12/337,796

(22) Filed: Dec. 18, 2008

(65) Prior Publication Data
US 2010/0157291 A1    Jun. 24, 2010

(51) Int. Cl.
*G01N 21/55* (2006.01)
*G01N 21/25* (2006.01)
*G01N 21/00* (2006.01)

(52) U.S. Cl. .................. 250/574; 356/410; 356/426

(58) Field of Classification Search .................. 250/226, 250/208.2, 578.1, 573, 574; 356/410, 411, 356/434, 435, 426, 427, 428
See application file for complete search history.

(56) References Cited

U.S. PATENT DOCUMENTS

| | | |
|---|---|---|
| 5,151,585 A | 9/1992 | Siebert |
| 5,324,401 A | 6/1994 | Yeung et al. |
| 5,370,842 A | 12/1994 | Miyazaki et al. |
| 5,445,934 A | 8/1995 | Fodor et al. |
| 5,631,734 A | 5/1997 | Stern et al. |
| 5,674,698 A | 10/1997 | Zarling et al. |
| 5,760,900 A | 6/1998 | Ito et al. |
| 5,793,485 A | 8/1998 | Gourley |
| 5,798,222 A | 8/1998 | Goix |
| 5,945,676 A | 8/1999 | Khalil et al. |
| 5,982,478 A | 11/1999 | Ainsworth et al. |
| 6,580,507 B2 | 6/2003 | Fry et al. |
| 6,628,390 B1 | 9/2003 | Johnson |
| 6,747,285 B2 | 6/2004 | Schueller et al. |

(Continued)

FOREIGN PATENT DOCUMENTS
WO    WO 99/54730 A1    10/1999

OTHER PUBLICATIONS

Singh, K., Liu, C., Capjack, C., Rozmus, W., an Backhouse, C.J., "Analysis of cellular structure by light scattering measurements in a new cytometer design based on a liquid-core waveguide", IEE Proc.-Nanobiotechnol., vol. 151, No. 1, Feb. 2004, pp. 10-16.

(Continued)

*Primary Examiner* — John Lee
(74) *Attorney, Agent, or Firm* — Hollingsworth & Davis, LLC

(57) ABSTRACT

Sensors can be used to obtain encoded sensing results from objects that have nonuniform relative motion. A photosensor or impedance-based sensor, for example, can obtain sensing results from objects that have relative motion within a sensing region relative to the sensor, with the relative motion being, for example, periodically varying, randomly varying, chirp-varying, or modulated relative motion that completes at least one modulation cycle within the sensing region. Relative motion can be caused by varying objects' speed and/or direction or by controlling flow of fluid carrying objects, movement of a channel, movement of a support structure, movement of a sensor, and/or pattern movement. A fluidic implementation can include shaped channel wall parts and/or a displacement component causing time-varying lateral displacement. A support structure implementation can include a scanner device and a rotary device that respectively control scanning and rotating movement of a movable support structure or of a sensor.

23 Claims, 13 Drawing Sheets

U.S. PATENT DOCUMENTS

| | | |
|---|---|---|
| 6,816,257 B2 | 11/2004 | Goix |
| 6,906,792 B2 | 6/2005 | Ortyn et al. |
| 7,034,933 B2 | 4/2006 | Walker et al. |
| 7,195,465 B2 | 3/2007 | Kane et al. |
| 7,195,797 B2 | 3/2007 | Mearini et al. |
| 7,252,360 B2 | 8/2007 | Hersch et al. |
| 7,277,569 B2 | 10/2007 | Bruce et al. |
| 7,298,478 B2 | 11/2007 | Gilbert et al. |
| 7,305,112 B2 | 12/2007 | Curry et al. |
| 7,355,699 B2 | 4/2008 | Gilbert et al. |
| 7,358,476 B2 | 4/2008 | Kiesel et al. |
| 7,420,677 B2 | 9/2008 | Schmidt et al. |
| 7,433,552 B2 | 10/2008 | Kiesel et al. |
| 7,440,101 B2 | 10/2008 | Auer et al. |
| 7,466,409 B2 | 12/2008 | Scherer et al. |
| 7,471,399 B2 | 12/2008 | Kiesel et al. |
| 7,479,625 B2 | 1/2009 | Kiesel et al. |
| 7,502,123 B2 | 3/2009 | Schmidt et al. |
| 7,522,786 B2 | 4/2009 | Kiesel et al. |
| 7,545,513 B2 | 6/2009 | Kiesel et al. |
| 7,554,673 B2 | 6/2009 | Kiesel et al. |
| 7,701,580 B2 | 4/2010 | Bassler et al. |
| 2004/0038386 A1 | 2/2004 | Zesch et al. |
| 2004/0067167 A1 | 4/2004 | Zhang et al. |
| 2007/0046301 A1 | 3/2007 | Kasapi |
| 2007/0076210 A1 | 4/2007 | Kiesel et al. |
| 2007/0146704 A1 | 6/2007 | Schmidt et al. |
| 2007/0147189 A1* | 6/2007 | Schmidt et al. ............ 369/13.47 |
| 2008/0181827 A1 | 7/2008 | Bassler et al. |
| 2008/0183418 A1 | 7/2008 | Bassler et al. |
| 2008/0186488 A1 | 8/2008 | Kiesel et al. |
| 2008/0186492 A1 | 8/2008 | Kiesel et al. |
| 2008/0186494 A1 | 8/2008 | Kiesel et al. |
| 2008/0186500 A1 | 8/2008 | Schmidt et al. |
| 2008/0186503 A1 | 8/2008 | Kiesel et al. |
| 2008/0186504 A1 | 8/2008 | Kiesel et al. |
| 2008/0186508 A1 | 8/2008 | Kiesel et al. |
| 2008/0187011 A1 | 8/2008 | Kiesel et al. |
| 2008/0197272 A1 | 8/2008 | Kiesel et al. |
| 2009/0190121 A1 | 7/2009 | Hegyi et al. |
| 2009/0194705 A1 | 8/2009 | Kiesel et al. |
| 2009/0195773 A1 | 8/2009 | Bassler et al. |
| 2009/0195852 A1 | 8/2009 | Bassler et al. |
| 2009/0220189 A1 | 9/2009 | Kiesel et al. |
| 2010/0157291 A1* | 6/2010 | Kiesel et al. ................. 356/244 |
| 2010/0261288 A1* | 10/2010 | Recknor et al. ............... 436/164 |

OTHER PUBLICATIONS

"Flow Cytometry", printed from www.wellscenter.iupul.edu/MMIA on Jan. 29, 2008, 4 pages.

Seamer, L.C., Kuckuck, F., and Sklar, L.A., "Sheath Fluid Control to Permit Stable Flow in Rapid Mix Flow Cytometry", Cytometry, vol. 35, 1999, pp. 75-79.

Office communication in U.S. Appl. No. 12/024,490, mailed Nov. 2, 2009, 14 pages.

Office communication in U.S. Appl. No. 11/698,409, mailed Nov. 17, 2009, 18 pages.

Office communication in U.S. Appl. No. 12/025,394, mailed Jan. 22, 2010, 7 pages.

Office communication in U.S. Appl. No. 12/023,436, mailed Feb. 5, 2010, 16 pages.

Amendment in U.S. Appl. No. 12/023,436, submitted Mar. 23, 2010, 24 pages.

Office communication in U.S. Appl. No. 12/023,436, mailed Apr. 16, 2010, 8 pages.

Amendment in U.S. Appl. No. 12/025,394, submitted Apr. 22, 2010, 17 pages.

Amendment in U.S. Appl. No. 11/698,409, submitted May 17, 2010, 16 pages.

Shapiro, H. M., Practical Flow Cytometry, Fourth Edition, Wiley-Liss, 2003, Table of Contents and pp. 49-59, 124-183, 191-197, 345, and 364-366.

Hoffman, R. A., "Flow Cytometry: Instrumentation, Applications, Future Trends and Limitations", Springer Series on Fluorescence, vol. 6, 2008, pp. 307-342.

Office communication in U.S. Appl. No. 12/023,436, mailed Dec. 23, 2008, 15 pages.

Amendment in U.S. Appl. No. 12/023,436, submitted Mar. 23, 2009, 22 pages.

Office communication in U.S. Appl. No. 12/022,485, mailed Jan. 16, 2009, 18 pages.

Amendment in U.S. Appl. No. 12/022,485, submitted Apr. 15, 2009, 30 pages.

Office communication in U.S. Appl. No. 12/024,490, mailed Dec. 24, 2008, 12 pages.

Amendment in U.S. Appl. No. 12/024,490, submitted Mar. 24, 2009, 32 pages.

Office communication in U.S. Appl. No. 11/698,409, mailed Jun. 11, 2010, 21 pages.

Office communication in U.S. Appl. No. 12/022,485, mailed Jul. 31, 2009, 5 pages.

Response to Restriction Requirement in U.S. Appl. No. 12/022,485, submitted Aug. 27, 2009, 20 pages.

Office communication in U.S. Appl. No. 12/023,436, mailed Jun. 12, 2009, 20 pages.

Amendment in U.S. Appl. No. 12/023,436, submitted Sep. 3, 2009, 29 pages.

Office communication in U.S. Appl. No. 12/024,490, mailed Jul. 22, 2009, 16 pages.

Amendment After Final Rejection in U.S. Appl. No. 12/024,490, submitted Sep. 22, 2009, 28 pages.

Office communication in U.S. Appl. No. 11/702,321, mailed Feb. 20, 2009, 19 pages.

Amendment in U.S. Appl. No. 11/702,321, submitted May 8, 2009, 21 pages.

Notice of Allowance and Fee(s) Due in U.S. Appl. No. 11/702,321 mailed Aug. 11, 2009, 20 pages.

Office communication in U.S. Appl. No. 11/702,320, mailed Aug. 12, 2009, 9 pages.

Office communication in U.S. Appl. No. 11/702,325, mailed Aug. 15, 2008, 14 pages.

Amendment in U.S. Appl. No. 11/702,325, submitted Nov. 17, 2008, 38 pages.

Office communication in U.S. Appl. No. 11/702,325, mailed Feb. 10, 2009, 8 pages.

Response with Terminal Disclaimer in U.S. Appl. No. 11/702,325, submitted May 5, 2009, 5 pages.

Office communication in U.S. Appl. No. 11/702,325, mailed Aug. 28, 2009, 13 pages.

* cited by examiner

CAUSING RELATIVE MOTION

The following applications, each of which is hereby incorporated by reference in its entirety, might be regarded as related to this application: "Sensing Photon Energies Emanating from Channels or Moving Objects", U.S. patent application Ser. No. 11/315,386, now published as U.S. Patent Application Publication No. 2007/0146704; "Method and System for Evaluation of Signals Received from Spatially Modulated Excitation and Emission to Accurately Determine Particle Positions and Distances", U.S. patent application Ser. No. 11/698,338, now published as U.S. Patent Application Publication No. 2008/0183418; "Method and System Implementing Spatially Modulated Excitation or Emission for Particle Characterization with Enhanced Sensitivity", U.S. patent application Ser. No. 11/698,409, now published as U.S. Patent Application Publication No. 2008/0181827; "Obtaining Information From Optical Cavity Output Light", U.S. patent application Ser. No. 11/702,249, now published as U.S. Patent Application Publication No. 2008/0186500; "Photosensing Optical Cavity Output Light", U.S. patent application Ser. No. 11/702,250, now published as U.S. Patent Application Publication No. 2008/0186503; "Distinguishing Objects", U.S. patent application Ser. No. 11/702,328, now published as U.S. Patent Application Publication No. 2008/0186488; "Encoding Optical Cavity Output Light", U.S. patent application Ser. No. 11/702,363, now published as U.S. Patent Application Publication No. 2008/0186492; "Moving Analytes and Photosensors", U.S. patent application Ser. No. 11/702,470, now published as U.S. Patent Application Publication No. 2008/0186504; "Obtaining Information from Time Variation of Sensing Results", U.S. patent application Ser. No. 12/022,485; "Providing Time Variation in Emanating Light", U.S. patent application Ser. No. 12/023,436; "Transmitting/Reflecting Emanating Light with Time Variation", U.S. patent application Ser. No. 12/024,490; "Producing Filters with Combined Transmission and/or Reflection Functions", U.S. patent application Ser. No. 12/025,394; "Sensing Photons From Objects in Channels", U.S. patent application Ser. No. 12/098,584, now published as U.S. Patent Application Publication No. 2008/0197272; "Obtaining Sensing Results Indicating Time-Variation", U.S. patent application Ser. No. 12/337,737; and "Obtaining Sensing Results and/or Data in Response to Object Detection", U.S. patent application Ser. No. 12/337,771.

BACKGROUND OF THE INVENTION

The present invention relates generally to techniques that cause an object or objects to have relative motion. For example, techniques can cause relative motion of objects within a sensing region relative to a sensor or sensing component such that the sensor or sensing component provides sensing results that indicate waveforms with time variation resulting from the relative motion.

U.S. Patent Application Publication No. 2008/0181827 describes techniques that use spatially modulated excitation/emission and relative movement between a particle and an excitation/emission pattern. For example, an interference pattern of excitation light with submicron periodicity perpendicular to particle flow can be used; other types of spatial modulation include a spatially modulated mask or micro-lens or micro-mirror array, electric or magnetic fields, acoustic field, molecular coating creating fluorescence quenching, and micro-cavity. As the particle moves along the pattern, emission is modulated according to the speed of the particle and the periodicity of the stripe pattern; examples of signals that may be used include periodic, chirped, and random signals. A single detector, which records emission over a couple of stripes, can be used. The signal can be recorded with fast detector readout to capture "blinking" of particles while moving through the excitation pattern. More generally, an environment can be provided along a channel that causes a particle to create a time modulated signal that is detected, such as by an optical array or electrode array, and evaluated. A system can also include means for providing relative movement between a particle and a spatially modulated excitation region; relative movement may be created by the particle moving, a detector/optical elements moving along, for example, the channel, or by movement of both. For example, a particle may be conveyed in a fluid, could be on a bio-chip, or could be suspended in a fluid and housed on a slide on the bed of a scanner with modulation patterns that move in substantially perpendicular directions. Techniques for evaluation of signals are described in U.S. Patent Application Publication No. 2008/0183418.

It would be advantageous to have improved techniques for causing objects to have relative motion within sensing regions.

SUMMARY OF THE INVENTION

The invention provides various exemplary embodiments, including systems, methods, and apparatus. In general, the embodiments involve causing nonuniform relative motion of objects within sensing regions.

These and other features and advantages of exemplary embodiments of the invention are described below with reference to the accompanying drawings.

DETAILED DESCRIPTION

Figure 1:
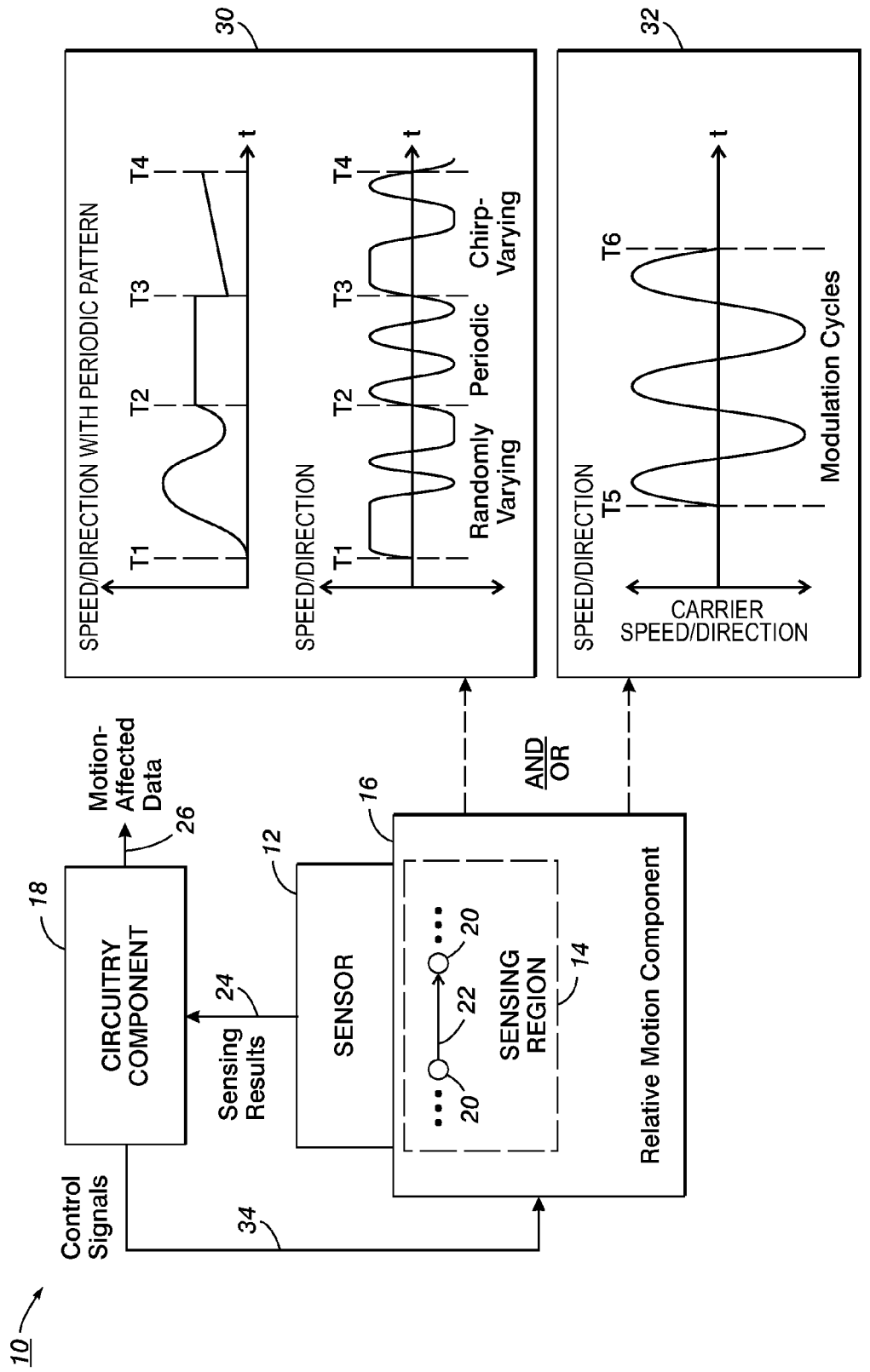
FIG. 1 is a schematic diagram illustrating general features of a system in which a relative motion component causes nonuniform relative motion of objects within a sensing region relative to a sensor.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

The term "sensing" is used herein in the most generic sense of obtaining information from a physical stimulus; sensing therefore includes actions such as detecting, measuring, and so forth. A "sensor" is a device that performs sensing. Data or other signals that indicate or include results of sensing are sometimes referred to herein as "sensing results". An operation "obtains" sensing results if the operation makes the sensing results available in any appropriate way in the context; for example, an operation could obtain sensing results by producing sensing results, by providing or transferring sensing results from one position or time to another, by accessing sensing results that are stored in computer memory or on a storage medium or captured in any other machine-accessible form, or in any other way appropriate to the context.

"Light" refers herein to electromagnetic radiation of any wavelength or frequency; unless otherwise indicated, a specific value for light wavelength or frequency is that of light propagating through vacuum. Light that can include information is sometimes referred to herein as an "optical signal".

"Photosensing" is sensing of light. A "photosensor" is accordingly an electronic device that performs photosensing. More specifically, if optical signals include information, a photosensor that receives the optical signals may be able to sense the information and provide sensing results that indicate or include the information; sensing results from a photosensor often indicate "photosensed quantities", meaning quantities that indicate a characteristic of photosensed light, such as an intensity, a spectral characteristic, etc. A surface at which photosensing occurs is referred to herein as a "photosensitive surface".

Another type of sensing relevant to some exemplary implementations described below is "impedance-based sensing", meaning sensing that obtains information from variation in resistance (or inversely, conductivity), capacitance, inductance, or another form of electrical impedance that varies in response to a physical stimulus such as an electrical or magnetic characteristic of an object or of an object's environment. As used herein, "impedance-based sensing" includes sensing with Hall effect sensors and similar types of sensors.

In general, the various types of sensors described herein provide sensing results in the form of electrical signals unless otherwise indicated or required by the context. The term "electrical signal" is used herein to encompass any signal that transfers information from one position or region to another in an electrical, electronic, electromagnetic, or magnetic form. Electrical signals may be conducted from one position or region to another by electrical or magnetic conductors, but the broad scope of electrical signals also includes light and other electromagnetic forms of signals and other signals transferred through non-conductive regions due to electrical, electronic, electromagnetic, or magnetic effects. In general, the broad category of electrical signals includes both "analog" and "digital" signals: An "analog" electrical signal includes information in the form of a continuously variable physical quantity, such as voltage; a "digital" electrical signal, in contrast, includes information in the form of discrete values of a physical characteristic, which could also be, for example, voltage.

In a system in which sensing is performed, an object moves relative to a region or component or feature of the system or "has relative motion" if the object has a succession of positions over time with respect to the region, component, or feature; the succession of positions is sometimes referred to herein as the object's "path", even though the object may not itself be moving in an absolute sense but only relative to the region, component, or feature. More generally, the term "path" is used herein in the general sense of a series of positions and/or configurations that a relatively moving and/or varying object can have during its relative motion and/or variation. For generality, a part of an object's relative motion, such as a part of a path, is sometimes referred to herein as a "segment", which could encompass any continuous series of one or more positions and/or configurations within the relative motion.

The various exemplary implementations described below address problems that arise in operating sensors to obtain sensing results from objects. For example, a number of techniques have been proposed in which sensing is performed during relative motion between objects and sensors to obtain time-varying sensing results. In general, previously proposed techniques employ some type of "uniform relative motion", a term used herein to refer to relative motion that has approximately constant speed and approximately constant direction, where the direction could be in a straight line or in a line that has approximately constant curvature such as an arc of a circle. Uniform scan motion and uniform rotating motion are two familiar types of uniform relative motion; as used herein, the term "scan motion" refers to relative motion substantially along a straight line, while "rotating motion" refers to relative motion substantially along a line of constant curvature, e.g. a circle or arc of a circle.

Although sensing with uniform relative motion can be performed in many ways, it is constrained by the requirement of uniformity: For example, if an object has uniform relative motion within an environment that is uniform in every other way, sensing results resulting from the object's relative motion will provide limited information because they will not in general include any time variation.

To increase information provided by sensing results, some techniques perform spatial modulation of sensing results using some sort of "patterned environment", a term used herein to mean an environment with a pattern that is present while several or many objects have relative motion within the environment; a patterned environment could result from a relatively stable or time-varying pattern in one or more of various features of the environment—excitation of objects in the environment, masking or filtering of light emanating from objects in the environment, impedance-based sensing of objects in the environment, photosensing of light emanating from objects in the environment, and so forth. Exemplary types of patterned environments described herein include random patterns, periodic patterns, and chirp patterns: As used herein regarding patterned environments, the term "random" refers to a pattern that is non-periodic over the entire length of a longitudinal sequence of regions; in contrast, a "periodic" sequence has at least one pattern that repeats more than once across the sequence's longitudinal length; and "chirp" sequences meet the above definition of random but can, with linearly varying time-scaling, meet the above definition of periodic, in effect being a sequence of periods of linearly changing frequency or wavelength.

Although uniform relative motion within a patterned environment can be used in various sensing techniques, a patterned environment must sometimes be quite complex in order to obtain desired sensing results. Also, although stable or time-varying patterned environments provide some flexibility, they can be difficult or expensive to fabricate or otherwise implement and have other practical limitations.

In these and other ways, uniform relative motion techniques are not sufficiently flexible and robust to provide all the types of sensing that would be useful.

In addressing the limitations of uniform relative motion techniques, exemplary implementations described below cause objects to have nonuniform relative motion within sensing regions. The general term "nonuniform relative motion" is used herein to refer to relative motion between a sensor or sensing component and an object in a sensing region relative to the sensor or sensing component, where the relative motion departs sufficiently from the above definition of "uniform relative motion" that it includes measurable variation in one or both of speed and direction; such variation is sometimes referred to herein as "speed/direction variation". In other words, nonuniform relative motion is relative motion between an object and a sensor or sensing component that departs measurably from having approximately constant speed in a direction that is a straight line or a line of approximately constant curvature line. Also, if an object and a sensor are not moving relative to each other, relative motion solely between the object and a patterned environment in a sensing region relative to the sensor would not, by itself, be an example of nonuniform relative motion as that term is used herein.

Nonuniform relative motion is "caused" when one or more things bring it about as an effect, with its "causes" being the things that bring about the nonuniform relative motion. Exemplary implementations described below illustrate various possible causes of nonuniform relative motions with various kinds of speed/direction variation; a specific nonuniform relative motion might be caused, for example, by a component, part, or other feature of a system, device, apparatus, or article of manufacture or by an act such as an operation of a component, part, system, device, apparatus, or article. By causing nonuniform relative motion, the exemplary implementations can overcome limitations of uniform relative motion techniques and can also provide new sensing techniques not previously available or proposed.

Operations that cause nonuniform relative motion can do so in a variety of ways. For example, an operation could "propel" or "drive" a fluid or other thing, meaning the operation applies force that imparts movement to or maintains movement of the fluid or other thing. Also an operation could "control" a flow or other movement or motion, meaning that the operation causes some sort of change in the flow, movement, or motion while it is occurring, acting as a concurrent cause of nonuniform relative motion. Or an operation could be performed in a way that "varies", meaning that something about the operation changes while it is being performed, again causing the nonuniform relative motion. In general terms, an operation could cause nonuniform relative motion by causing other effects that, together, result in the nonuniform relative motion. For example, an operation could cause speed/direction variation in an object's relative motion within a sensing region; a mechanism that performs such an operation is sometimes referred to herein as a "motion-varying mechanism".

Although nonuniform relative motion can have any of a multitude of types of speed/direction variation, the types of speed/direction variation that are described below in relation to exemplary implementations include periodically varying, randomly varying, and/or chirp-varying relative motion. These types are applicable to a variety of implementations, including, for example, implementations in which sensing results include only information resulting from speed/direction variation and also including implementations in which sensing results include information both from speed/direction variation and also from a patterned environment, such as an excitation, filtering, or sensing pattern. As used herein, nonuniform relative motion within a sensing region is "periodically varying" if the sensing results are periodic, i.e. they include at least one pattern that repeats more than once within the sensing region; in contrast, nonuniform relative motion is "randomly varying" if it is not periodically varying; and randomly varying nonuniform relative motion is "chirp-varying" if the sensing results can be linearly time-scaled to obtain periodic sensing results. All these types of variation can be implemented in various ways, such as in fluidic implementations and/or implementations in which objects are on support structures.

An object's relative motion, if it approximates or is similar to a straight, curving line, or other line without sharp angles or other vertex-like changes of direction, is treated herein as providing a directional orientation as follows: A direction parallel or approximately parallel to the motion is sometimes referred to as a "longitudinal" or "lengthwise" direction, while a direction perpendicular or approximately perpendicular to the path is sometimes referred to as a "radial", "lateral", or "transverse" direction. The lengthwise direction in which the object is moving is sometimes referred to as "forward" or "downstream", while the opposite direction is sometimes referred to as "backward" or "upstream". A radial direction away from the object's path is "out" or "outward", while a radial direction toward its path is "in" or "inward". Light propagating toward the path may be referred to as "incoming" or "incident", while light propagating away from the path may be referred to as "outgoing". A component or arrangement of components is "along" the path if it is disposed near the path and has some extent in a longitudinal direction. A component or arrangement of components is "around" the path if, in a plane transverse to the path, it intersects multiple radial directions, at least two of which are separated by approximately 180 degrees of arc. In general, it should be understood that the above directional orientation is arbitrary and only for ease of description, and that an object's relative motion may have any appropriate orientation.

In a fluidic implementation in which fluid carries objects in a longitudinal direction in a channel, channel walls can have inner surfaces with shapes that cause the relative motion to be nonuniform; in the specific example of "microfluidic channels", i.e. fluidic channels with cross-sectional dimensions between approximately 1.0 mm and 0.1 µm, the Reynolds number is extremely low so that flow remains laminar in a direction parallel to channel walls, without turbulence despite changes in direction and/or speed resulting from channel wall shapes. In exemplary implementations described below, nonuniform relative motion caused by shaped inner surfaces of channel walls can be periodically varying, randomly varying, or chirp-varying. A region of a channel with wall shapes that cause nonuniform relative motion is sometimes referred to herein as a "shaped-wall region".

In another fluidic technique, a displacement component can cause time-varying relative displacement of objects in lateral directions not parallel to the longitudinal direction; the lateral relative displacement could be periodically varying, randomly varying, or chirp-varying. Similarly, in implementations in which objects are on support structures, motion of one or both of a support structure and a sensor can be controlled to produce periodically varying, randomly varying, or chirp-varying relative motion. In both of these cases, whether with a displacement component or with controlled movement of a support structure and/or sensor, additional types of nonuniform relative motion can be caused, as described below in relation to exemplary implementations.

Modulated relative motion is one such additional type of nonuniform relative motion. The term "modulated relative motion" is used herein to refer to motion that includes modulation cycles in combination with other relative motion of one or more appropriate types; the other relative motion could be referred to as a "carrier component" by analogy to a carrier frequency in signal modulation techniques, and could, for example, be uniform relative motion such as scan motion or rotating motion. The term "modulation cycle" is used herein to refer to a single period-like portion of wave-like speed/direction variation, such as a portion between two maxima, between two minima, or between two non-extrema that have the same phase in relation to nearby extrema—just as each cycle of a sinusoidal wave is equal to one period, so each cycle of modulation is a period-like portion of wave-like speed/direction variation. Frequency, wavelength, and/or amplitude could, however, vary during a single modulation cycle or between different modulation cycles. In general, the modulation techniques described below complete at least one modulation cycle within the sensing region, making it possible to extract information about frequency, wavelength, and/or amplitude of modulation from an object's relative motion within the sensing region.

In any of the exemplary implementations, the sensing results can indicate at least one time-varying waveform with information resulting from the nonuniform relative motion. More specifically, the sensing results can include motion-encoded information resulting from the nonuniform relative motion. The sensing results can, for example, indicate at least one waveform with time variation resulting from the nonuniform relative motion. The sensing results can be used to obtain data indicating information resulting from the nonuniform relative motion, such as by operations of a processor or processing component.

Also, in some exemplary implementations, a relative motion component includes one or more of a motion device, a fluidic device, a scanner device, and a rotary device that, in response to control signals, can provide time-varying displacement. A scanner device, for example, can provide relative motion in a scanning direction between a support structure supporting one or more objects and an encoder/sensor; in response to an object's trigger signal, the scanner device can provide time-varying displacement in one or more of three directions, including the scanning direction, a first lateral direction in which distance between encoder/sensor and the object is not changed, and a second lateral direction in which distance between encoder/sensor and the object changes.

Similar, a rotary device can provide relative motion in a direction of rotation between a support structure supporting one or more objects and an encoder/sensor; in response to an object's trigger signal, the rotary device can provide time-varying displacement in one or more of three directions, including the rotation direction, a radial direction in which distance between encoder/sensor and axis of rotation changes, and a lateral direction in which distance between encoder/sensor and the object changes.

By providing these capabilities, the exemplary implementations alleviate the limitations of uniform relative motion techniques, such as those using patterned environments; for example, some implementations can employ uniform excitation and filtering in combination with a relative motion component, avoiding difficulties in fabricating or otherwise obtaining appropriate components that provide patterned excitation and/or filtering. Further, some exemplary implementations provide new types of encoding/sensing not previously known.

The exemplary implementations described herein could also be modified or operated in various other ways. For example, they could cause other types of nonuniform relative motion besides the specific examples described herein, such as further combinations of the specific types described.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry, and a given hardware component can similarly be replaced by equivalent processor operations controlled by software.

Circuitry can be described based on its operation or other characteristics. For example, circuitry that performs control operations is sometimes referred to herein as "control circuitry" and circuitry that performs processing operations is sometimes referred to herein as "processing circuitry".

FIG. 1 shows general features of techniques that cause nonuniform relative motion within a sensing region relative to a sensor. The techniques are illustratively implemented in system 10, but could be similarly implemented in various apparatus and methods. System 10 illustratively includes sensor 12, sensing region 14, relative motion component 16, and circuitry component 18.

As used herein, the term "system" refers to a combination of two or more parts or components that can perform an operation together. A system may be characterized by its operation. A system may include one or more parts or components that can operate automatically, but, as used herein, the term "system" can include a system with components that operate non-automatically, automatically, partially automatically, or any combination.

Within a system, apparatus, device, or other article, components and parts may be referred to in a similar manner. In addition to sensors as defined above, other components of a system, for example, can include a "relative motion component" that operates to cause some sort of relative motion. Various other components that can occur in a system that includes sensors are also identified by their operations, including "excitation components", "displacement components", "filter components", and "sensing components" as described below. In addition, a component or part may be identified by characteristics other than its operation; for example, a "circuitry component" is a component that includes circuitry.

The term "excitation component" refers herein to a part or component that provides excitation of any appropriate type, in response to which objects emanate light. For example, illumination of various kinds can cause objects to emanate light, i.e. to photoluminesce, so that many excitation components are light sources; another example of excitation is an electron beam that causes objects to emanate light, i.e. to cathodoluminesce. Other types of excitation can also be provided, within the scope of the techniques described herein, and further examples of excitation are described in co-pending U.S. patent application Ser. No. 12/023,436, entitled "Producing Time Variation in Emanating Light" and incorporated herein by reference.

The term "displacement component" refers herein to a part or component that provides displacement of any appropriate type, typically displacement of objects having relative motion within a sensing region; displacement that is part of relative motion is sometimes referred to herein as "relative displacement". Although a relative motion component could be thought of as a type of displacement component, a given system might include both a relative motion component and a displacement component or might include a single device that can operate both as a relative motion component and as a displacement component, and a relative motion component might include one or more displacement components that each provide a respective type of relative displacement; exemplary implementations described below illustrate some of these possibilities. For example, a fluidic device could operate as a relative motion component, providing an object's relative motion in a longitudinal direction within a channel, and a motion device could operate as a displacement component, causing the channel walls along a sensing region to move relative to the object such as in a lateral direction not parallel to the longitudinal direction. Or a scanner or rotary device could operate as a relative motion component providing an object's relative motion in a scanning direction or in a direction of rotation, and could also operate as a displacement component providing relative displacement during the object's relative motion within a sensing region.

The term "optical filter" or simply "filter component", "filter", or "mask" refers herein to a light-transmissive part or component that transmits light in accordance with a respective criterion, sometimes referred to herein as a filter's "type". For example, one general category of filters is "band pass filters", referring to types of filters that, across some application's range of photon energies, e.g. a range of wavelengths or frequencies such as the visible range, preferentially transmit light within a subrange, sometimes referred to as a "band"; a band pass filter's type can therefore be specified by specifying the band or subrange of photon energies in which it transmits. A "blocking filter", which does not transmit any light in an application's range, can be viewed as a band pass filter with a band of zero bandwidth, while a "transparent filter", which transmits all light in an application's range, can be viewed as a band pass filter with a band that includes the entire range. Other types of filters can also be provided, within the scope of the techniques described herein, and further examples of filters are described in co-pending U.S. patent application Ser. No. 12/024,490, entitled "Transmitting/Reflecting Emanating Light with Time Variation" and incorporated herein by reference.

The term "sensing component" refers herein to a sensor, as described above, or to a component that includes a sensor together with at least some related circuitry. As with other types of patterned environments, sensing components can be categorized in relation to sensing patterns, some examples of which are described below. In general, categories of sensing patterns can include, for example, periodic patterns, chirp patterns, random patterns, and so forth, and various other categories could be identified; techniques employing sensing patterns are described in more detail in co-pending U.S. patent application Ser. No. 12/337,737, entitled "Obtaining Sensing Results Indicating Time-Variation" and incorporated herein by reference in its entirety.

In the example illustrated in FIG. 1, sensor 12 responds to object 20 in sensing region 14, obtaining sensing results from object 20 and providing the sensing results to circuitry component 18.

In this context, the term "region" refers to a connected set of points or positions in space. In the particular examples, sensing region 14 is a region that is "relative to" a component or device, meaning that the region has an approximately constant spatial relationship to the component or device and accordingly would move with the component or device if the component or device moved; more specifically, sensing region 14 is a region relative to sensor 12, as suggested in FIG. 1 by its position adjacent sensor 12. Region 14 may be thought of as the region relative to sensor 12 within which an object can interact with sensor 12 such that information can be sensed through the interaction to an appropriate level of accuracy for a given application.

In embodiments described herein, objects move into and out of regions, from one region into another, and within regions. Accordingly, regions as described herein are not in general bounded by structures that would interfere with such movements, but each sensing region could have geometrically defined, imaginary boundaries within which a given level of accuracy can be obtained by the respective sensor.

Sensor 12 could perform sensing by interacting with object 20 in various ways. For example, light could emanate from object 20, such as by emission, scattering (including, e.g. reflection), or transmission, and a portion of the emanating light could be received by photosensors in sensor 12. In general, such emanating light includes light within an application's range of photon energies, meaning that techniques as in FIG. 1 can be successfully used in a given application, e.g. flow cytometry, bio-chip readout, scanning of a support structure bearing spots or other objects, or any suitable kind of analyte detection, even though emanating light might also include photon energies that are outside the application's range and that might not interact with photosensors in sensor 12 in the same way as light in the application's range. In other examples, object 20 could interact electrically or magnetically with impedance-based sensing elements in sensor 12. In general, a sensor of any kind obtains sensing results "from" objects in a sensing region when the sensing results include information resulting from any such interaction between the sensor and the objects while the objects are in the sensing region.

The term "object" is used herein in the general sense of any thing from which a sensor can obtain information. In contexts with more than one object, the term "distinguishable object" is used herein to refer only to an object that is configured relative to other objects and/or has other characteristics such that the sensor being used can obtain information from the object substantially separately from information obtained from other objects. For example, if objects in a set are approximately the same in speed, mass, structure, etc. and therefore would not be distinguishable if more than one were concurrently present in a given sensing region, the objects in the set may nonetheless be distinguishable if they are sufficiently separated in position that only one of them at a time can be in a given sensing region. Where a distinction between a sensor's distinguishable and non-distinguishable objects in a given implementation can be described in terms of a parameter, such as extent of separation of position, the distinction may be referred to as a "resolution limit" of the sensor.

In some implementations, sensors can obtain information about objects by receiving signals from them; for example, signals in the form of light can emanate from an object, whether through emission (e.g. radiation, fluorescence, incandescence, chemoluminescence, bioluminescence, cathodoluminescence, other forms of luminescence, etc.), elastic or inelastic scattering (e.g. reflection, deflection, diffraction, refraction, etc.), or transmission, and can be sensed by a photosensor. The light "emanates from" or is simply "from" the object, and may be referred to herein as "emanating light". An object from which light is emanating may be referred to herein as a "light-emanating object". In other implementations, sensors can obtain information about objects in other ways, some of which are mentioned herein; in particular, impedance-based sensors can obtain information about objects in various ways, resulting from, for example, interactions between objects and an arrangement of electrodes or an arrangement of Hall effect sensors.

Examples of objects that could occur in implementations as described below include droplets, small volumes of fluid, single molecules, agglomerated molecules, molecule clusters, cells, viruses, bacteria, lengthy polymers such as DNA or protein chains, submolecular complexes such as tags on DNA or protein chains, microparticles, nanoparticles, beads or other small particles that can bind and carry specific chemicals or other analytes, emulsions, any such type of object on a support structure such as a slide or in an array such as an array of sample wells, and a distinguishable region of a surface such as a small area of a sheet of paper or other image-bearing medium; a distinguishable surface region, could, for example, be a colored spot. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be a "scattering component" of a droplet. An analyte (i.e. a chemical species being investigated) in a droplet or other object can act as a fluorescent, absorbent, or scattering component. Analyte that is otherwise homogeneously distributed, for example, can be localized by binding to carrier beads, resulting in a moving object that emanates light or provides other signals in a way that depends on the analyte.

With respect to a light-emanating object, the expressions "characteristic of an object" and "emanating light including information" have related meanings: The term "characteristic" refers to a trait, quality, or property of an object that can be measured and that persists with a given value or within a given range or other subset of possible values while light that "includes information about the characteristic" is emanating from the object. In appropriate implementations, characteristics of an object could include mass, volume, density, cross-section or other shape, chemical composition, position, speed, acceleration, direction of movement, spin axis, directional or angular velocity or momentum, net charge, charge polarity, absorption spectrum, emission spectrum, scattering spectrum, and so forth. Therefore, emanating light "includes" information about a characteristic of an object if information included in the emanating light indicates a value, range, or other measure of the characteristic. Similar terminology can apply to types of interactions other than emanating light and to information of other types that can be included in light emanating from an object or that can be detected or sensed from other types of interactions, such as interactions with impedance-based sensors; some exemplary implementations described herein relate to other types of interactions and other types of information.

Emanating light or signals resulting from other types of interactions can "include information" in many ways, some of which are described below in relation to specific implementations. Various criteria could be used to determine whether emanating light or a signal resulting from another type of interaction includes specified information, and such criteria can be referred to as "encoding criteria". Some encoding criteria, for example, involve comparison of magnitude of a signal with noise magnitude, e.g. signal-to-noise (S/N) ratios, because S/N ratio can affect whether specified information can be recovered from sensing results obtained by photosensing emanating light. Other types of encoding criteria could be used as appropriate. Where emanating light or a signal resulting from another type of interaction satisfies an appropriate encoding criterion for specified information, the light or signal may be said to "encode" the information.

Similarly, sensing results, whether from photosensing emanating light, from impedance-based sensing (e.g. with electrodes or Hall effect sensors), or from another type of sensing, can "include information" in many ways, and similar encoding criteria could be applied as with signals. Where sensing results indicate one or more time-varying waveforms, the sensing results can be referred to as having "encoded time variation" or as "indicating time variation". As implied above, sensing results that include encoded time variation or other types of encoded information are sometimes referred to herein as "encoded sensing results" to distinguish from sensing results that might not be encoded. If the encoded information results from relative motion of objects, the sensing results or time variation that include the information may be referred herein as "motion-encoded", and the information itself may also be described as "motion-encoded information".

The term "waveform" is used herein in the general sense of any set of values that varies over one or more dimensions, whether continuous or discrete, whether analog or digital, and whether measured or obtained in any other way; a "time-varying waveform" is a waveform that varies over a time dimension. Some of the time-varying waveforms described below in relation to exemplary implementations include intensity values, but the expression "time-varying waveforms" also encompasses other values that vary over time, including purely numerical values with no specified units or other physical significance. A "sensed time-varying waveform" is a time-varying waveform that is indicated by sensing results obtained over time. For example, if a photosensor provides sensed quantities that indicate intensity of received light, its sensing results could indicate a time-varying waveform indicating intensity sensed over time.

In general, information in a time-varying waveform could result from an object's relative motion within a sensing region in any of various ways, some of which are described below in relation to exemplary implementations. For example, an object could move relative to a sensor or to one or more parts or components of a sensor or relative to one or more patterns or other features provided within or relative to a sensing region such that information about the object's relative motion, e.g. about relative speed or other relative rate of displacement, can be included in emanating light or in other signals resulting from interaction between the object and the sensor and can therefore be included in encoded sensing results. An object that has relative motion within a sensing region is sometimes also referred to herein as "moving" or as having "motion" or "movement", but an object's relative motion within a sensing region may result from any appropriate motion of the object and/or motion of a sensor, its parts or components, or patterns or other features within or relative to its sensing region, such as a pattern of excitation, filtering, or sensing or another environmental pattern or feature.

In FIG. 1, relative motion component 16 causes motion of object 20 and other objects (not shown), and the relative motion of object 20 includes a segment of relative motion within region 14, indicated by arrow 22. Arrow 22 is shown extending in a longitudinal direction, but this is only illustrative; the segment of relative motion within region 14 could have any appropriate shape, speed, and/or direction, as suggested by some of the exemplary implementations described below. Relative motion component 16 could also, of course, cause relative motion of object 20 into and out of region 14, also suggested by some of the exemplary implementations described below.

As illustrated by arrow 24, sensor 12 obtains sensing results from object 20, and the sensing results can illustratively take the form of electrical signals provided to circuitry component 18. The sensing results could include information resulting from relative motion of object 20; for example, they could indicate one or more time-varying waveforms with information resulting from the nonuniform relative motion of object 20 within region 14. If they include such information, the sensing results would be an example of motion-encoded sensing results as described above, and circuitry component 18 could, for example, perform processing operations that use the sensing results to obtain data that also include the encoded information, such as by also indicating time-varying waveforms; for such an implementation, circuitry component 18 might include a microprocessor or other processor or central processing unit (CPU), which could be programmed to perform the processing operations. Circuitry component 18 could provide the data for further operations or for storage or transmission, as suggested by arrow 26. Sensing results from sensor 12 could, however, take various other forms and motion-affected sensing results and data could be used in various other ways.

Encoded sensing results or data that indicate a time-varying waveform with information resulting from an object's relative motion within a sensing region are also sometimes referred to herein as "motion-affected" sensing results or data, as illustrated by the label adjacent arrow 26. Motion-affected sensing results and/or data can be used in many ways, some of which are described below in relation to exemplary implementations. For example, motion-affected sensing results or data can be used to obtain data indicating some or all of the encoded information, an operation referred to as a "decoding" operation. The results of decoding can be used to distinguish objects and in various other ways, some of which are described below in relation to exemplary implementations. In exemplary applications, such as where distinguished objects are registration marks in documents or other images, appropriate subsequent operations can be controlled based on results of operations that distinguish objects.

The graphs in boxes 30 and 32 in FIG. 1 illustrate several types of nonuniform relative motion of object 20 that relative motion component 16 could cause, such as in response to control signals from circuitry component 18 as illustrated by arrow 34 or in other ways. In each of the graphs, the horizontal axis represents time and is labeled "t, while the vertical axis abstractly represents one or both of speed and direction, with speed and/or direction varying over time during the nonuniform relative motion. In the illustrated examples, relative motion component 16 operates as a "motion-varying mechanism", meaning a mechanism that varies one or both of speed and direction of objects' relative motion within sensing region 14 and that therefore can operate to cause nonuniform relative motion. Exemplary implementations described below cause nonuniform relative motion by varying speed and direction in a number of specific ways, thus illustrating specific examples of motion-varying mechanisms.

The graphs in box 30 illustrate examples of three types of nonuniform relative motion described above, i.e. randomly varying, periodically varying, and chirp-varying relative motion. The upper graph illustrates speed/direction variation in an environment that also includes a periodic pattern that encodes sensing results; the periodic pattern could, for example, be an excitation pattern, a filter pattern, or a sensing pattern. The lower graph, on the other hand, illustrates speed/direction variation that follows cycles, referred to below as "speed/direction cycles". As explained below, the time scales of the two graphs are related.

In the illustrative waveform in the upper graph in box 30, speed/direction varies along a curve between times T1 and T2 in such a way that sensing results (not shown) that encode information from the periodic pattern are non-periodic; therefore, this portion of the waveform illustrates an example of randomly varying relative motion. Then, between times T2 and T3, speed/direction holds constant and does not vary, so that the encoded sensing results (not shown) due to the periodic pattern are periodic; because speed/direction is constant, however, this is an example of uniform relative motion, not periodically varying relative motion. Finally, between times T3 and T4, speed/direction increases linearly, so that the encoded sensing results (not shown) are non-periodic but can be made periodic with appropriate linear time-scaling; therefore, this portion of the waveform illustrates randomly varying relative motion that is, more specifically, chirp-varying relative motion.

In the illustrative waveform in the lower graph in box 30, speed/direction variation follows cycles between times T1 and T2 but does not include a periodically repeating pattern of cycles, so that the sensing results (not shown) that encode information from the nonuniform relative motion are also non-periodic; therefore, this portion of the waveform illustrates another example of randomly varying relative motion. Then, between times T2 and T3, speed/direction follows two cycles that are approximately identical, so that the encoded sensing results (not shown) are periodic; therefore, this is an example of periodically varying relative motion in contrast with the uniform relative motion between times T2 and T3 in the upper graph. Finally, between times T3 and T4, speed/direction follows cycles of increasing frequency and decreasing wavelength such that the encoded sensing results (not shown) are non-periodic but can be made periodic with appropriate linear time-scaling; therefore, this portion of the waveform illustrates another example of chirp-varying relative motion.

The graph in box 32 illustrates modulated relative motion, another type of nonuniform relative motion described above. In this graph, the horizontal axis crosses the vertical axis at a value labeled as the "carrier speed/direction", meaning that it is uniform relative motion that serves as a carrier component as described above. In addition, between times T5 and T6, the graph includes modulation cycles, illustratively 2.5 cycles, i.e. more than one modulation cycle is completed within sensing region 14. Although the modulation cycles in box 32 are relatively regular, frequency, wavelength, and/or amplitude could vary during a single modulation cycle or between different modulation cycles, as noted above. Because at least one modulation cycle is completed in the illustrated example, it is possible to extract information about frequency, wavelength, and/or amplitude of modulation from sensing results provided by sensor 12.

As suggested by the words "AND/OR" between the arrows leading from relative motion component 16 to boxes 30 and 32, the illustrated examples of nonuniform relative motion are not mutually exclusive, but rather could be concurrently caused in a given example of nonuniform relative motion. For example, the modulation cycles in box 32 could be caused with any of the relative motion types shown in the lower graph in box 30. Also, two or more of the types of nonuniform relative motion in box 30 could be superimposed by causing them concurrently, such as with different types of speed/direction variation that can be independently caused; further, different types of cyclic variation as in the lower graph in box 30 could be caused in sufficiently different frequency bands that they would provide independent information encoding. It would also be possible, of course, to combine any of these examples with any appropriately patterned environment to obtain additional types of nonuniform relative motion.

Components of system 10 can be implemented in any appropriate way, and some exemplary implementations are described below. Each of sensor 12, relative motion component 16, and circuitry component 18 could take a wide variety of different forms, illustrative examples of which are described below. For example, each of the below-described exemplary implementations involves relative motion within a sensing region, but relative motion component 16 can cause relative motion in many different ways, producing, for example, one or both of fluidic relative motion and support-based relative motion. In general, sensor 12 can be any suitable type of sensor such as a photosensor or an impedance-based sensor. Also, encoded sensing results can initially take the form of analog or digital electrical signals, depending on the structure and circuitry included in sensor 12, but encoded sensing results could be converted to other forms, such as optical or other electromagnetic signals, such as for subsequent storage, transmission, and processing; additional examples of sensing techniques are described in co-pending U.S. patent application Ser. No. 12/337,737, entitled "Obtaining Sensing Results Indicating Time-Variation" and incorporated herein by reference in its entirety.

Figure 2:
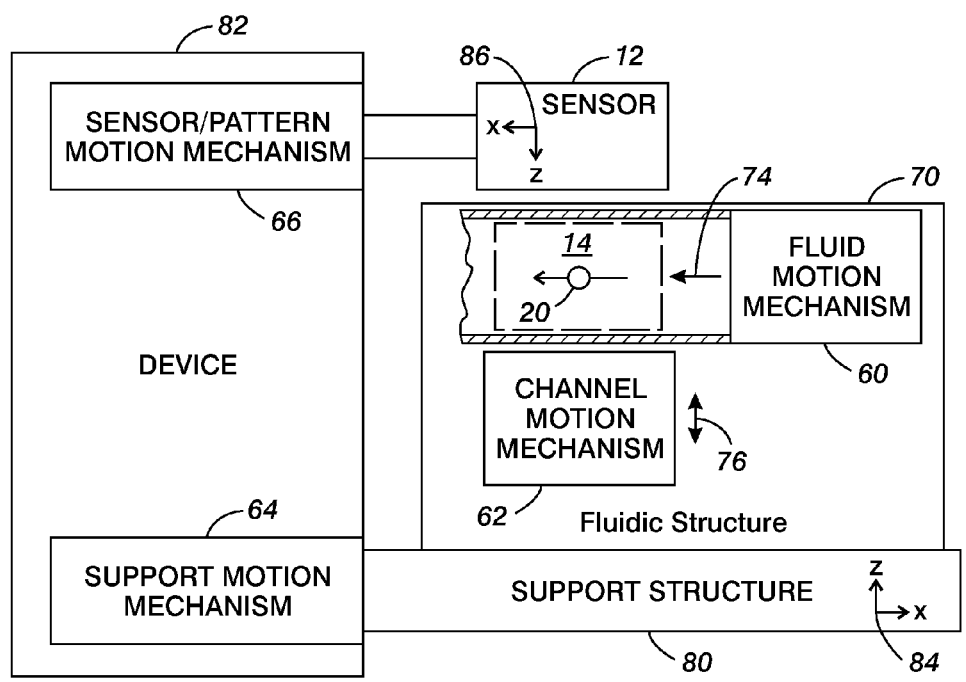
FIG. 2 is a schematic diagram showing general features of implementations of systems as in FIG. 1 with several mechanisms that control movement.

FIG. 2 shows a schematic representation of relative motion component 16, with several examples of types of mechanisms it could include, illustratively fluidic motion mechanism 60, channel motion mechanism 62, support motion mechanism 64, and sensor/pattern motion mechanism 66. Each of the illustrated types of mechanisms could be a motion-varying mechanism that participates in causing nonuniform relative motion, as illustrated by some of the exemplary implementations described below, and other types of mechanisms could also be employed in causing nonuniform relative motion.

Fluidic motion mechanism 60 and channel motion mechanism 62 are illustratively shown within fluidic structure 70; as used herein, the terms "fluidic structure" and "fluidic device" refer respectively to a structure or device that depends for its operation on fluid positioning or fluid flow. In general, the term "fluid" is used herein to encompass all media that can flow, including liquids, gases, aerosols, and so forth. The related term "channel" refers herein to any tube or other enclosed passage within a fluidic structure through which fluid flows during operation. In order to contain fluid, a channel or other fluidic region is typically "bounded", meaning that surfaces or surface areas bound it on at least some sides. In the illustrated example, channel walls 72 have inner surfaces that bound a channel within fluidic structure 70.

Fluidic motion mechanism 60 operates to control flow of fluid carrying objects within sensing region 14, which is in the channel bounded by walls 72. The flow of fluid within the channel is represented by arrow 74; as described above, arrow 74 can be treated as a longitudinal direction. Fluidic motion mechanism 60 could, for example, include one or more fluidic propulsion devices such as pumps together with circuitry that can control the pumps in response to appropriate control signals, so that the pumps in turn control flow of fluid within sensing region 14.

Channel motion mechanism 62 operates to control movement of the channel bounded by walls 72. Mechanism 62 can, for example, include one or more suitable motion devices that operate to move walls 72 in lateral directions that are not parallel to the longitudinal direction, as suggested by bidirectional arrow 76. Mechanism 62 can also include appropriate circuitry that responds to control signals by controlling operation of the motion devices so that they in turn control movement of the channel. As the channel moves in a lateral direction, objects being carried by fluid through sensing region 14 have additional relative motion in a direction opposite the lateral direction.

In the illustrated implementation of relative motion component 16, fluidic structure 70 is supported on support structure 80, which is in turn connected to device 82. Device 82 includes mechanisms 64 and 66, and is also connected to sensor 12.

Support motion mechanism 64 operates to control movement of support structure 80. Mechanism 64 could be implemented with a combination of one or more motion devices together with appropriate circuitry that responds to control signals by controlling operation of the motion devices. The motion devices could cause relative motion, as suggested by x- and z-axes 84. Although shown in combination with fluidic structure 70 and mechanism 60 and 62, relative motion component 16 could also be implemented in systems in which objects are supported more directly on support structure 80.

Sensor/pattern motion mechanism 66 similarly operates to control movement of sensor 12, of one or more parts or components within it, or of a pattern within or relative to sensing region 14, and could similarly include one or more motion devices together with appropriate circuitry that responds to control signals by controlling operation of the motion devices. As suggested by x- and z-axes 86, the motion of sensor 16 and of support structure 80 can combine to provide a given relative motion; in other words, motion of sensor 12 in its x-direction is equivalent to motion of support structure 80 in its x-direction, while motion of sensor 12 in its z-direction is equivalent to motion of support structure 80 in its z-direction, even though the respective x-directions and z-directions are shown as opposites.

As indicated by some of the exemplary implementations described below, device 82 could, for example, be a scanner device or a rotary device. As explained in greater detail below, such a device could provide a carrier component of relative motion as well as modulation cycles as described above in relation to FIG. 1.

Fluidic structure 70 together with mechanisms 60 and 62 are only one example of how relative motion of objects could be subject to displacement control as the objects follow respective paths through a sensing component with one or more sensors in an appropriate arrangement. More generally, a variety of different displacement control arrangements could be used along paths of objects that have relative motion into, out of, and within each of a series of sensing regions.

Figure 3:
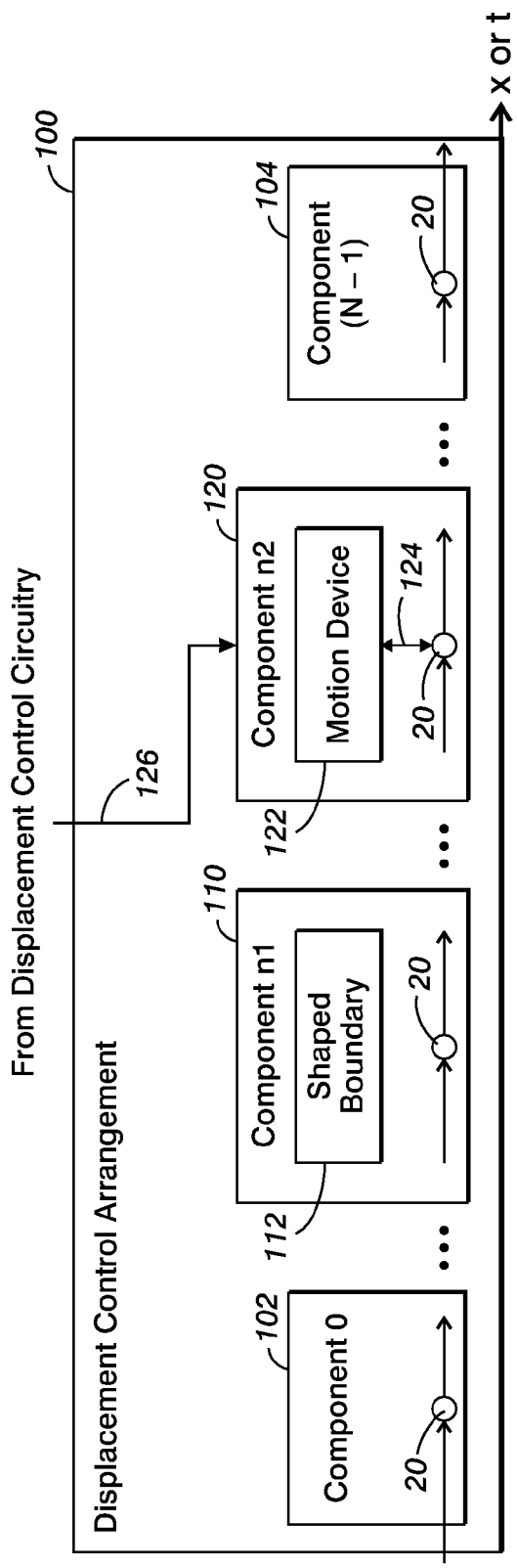
FIG. 3 is a schematic diagram showing features of exemplary displacement control arrangements that can cause nonuniform relative motion.

In FIG. 3, displacement control arrangement 100 is along a path of object 20 which has relative motion into, out of, and within a series of sensing regions, each relative to a respective sensor or sensing component. Displacement control arrangement 100 includes a combination of one or more displacement control components, each of which is illustratively shown enclosing a respective segment of the path of object 20 as it has relative motion within sensing regions. It would, of course, be possible to implement displacement control components in other ways, such as where an object has relative motion along a path that is not enclosed within a channel or fluidic structure. Further, as described above, relative motion of object 20 could be produced by any of a wide variety of types of motion control, including any of those described in relation to FIG. 2.

Although displacement control components could be positioned in any appropriate way along a path, the displacement control components in FIG. 3 are arranged along a one-dimensional coordinate axis labeled the "x OR t" axis. As suggested by this label, the path of object 20 can be treated either as extending in space, such as along an x-direction, or as occurring over time, t: In some cases specifically indicated in this application, the x-direction thus refers solely to an object's path, which might not follow a straight or constantly curved line relative to the environment; in some other cases, however, the x-direction refers to a longitudinal direction in which fluid is caused to flow in a fluidic channel, a scanning direction in which relative motion is caused by a scanning device, or a rotating direction in which relative motion is caused by a rotary device. Where the x-direction refers solely to an object's path, information about its speed or other rate of displacement can be sufficient to allow an approximate mapping between its x-direction positions and times t, more generally, mapping between an object's x-direction positions and times t can be based on any suitable system, such as with trigger detection techniques as described in U.S. Pat. No. 7,358,476, entitled "Sensing Photons from Objects in Channels", and in co-pending U.S. patent application Ser. No. 12/337,771, entitled "Obtaining Sensing Results and/or Data in Response to Object Detection", both incorporated herein by reference in their entireties, or from other techniques, including obtaining information such as a trigger signal from an object's encoded signal. In general, however, trigger detection is not necessary for exemplary implementations described herein, except as otherwise indicated, because sensing results indicating time variation can be obtained in response to relative motion of objects within an encoding/sensing region that has a fixed pattern or environment.

FIG. 3 shows several exemplary components within a sequence of control components 102 through 104, with component 102 labeled "0" and component 104 labeled "(N−1)". Although each displacement control component in the sequence illustratively contains a respective segment of the path, it may be possible to implement displacement control components that affect displacement in overlapping segments of a path or that interact in other ways.

Control component 110, labeled "n1", illustratively includes shaped boundary 112, meaning that a boundary that extends partially or completely around the path, such as the boundary of a fluidic channel, has a shape that affects or controls displacement of object 20 as it has relative motion along the path, such as by affecting its speed or other rate of displacement. Several examples of boundary shapes are described below in relation to exemplary implementations.

Control component 120, labeled "n2", illustratively includes motion device 122. Similarly to channel motion mechanism 62 in FIG. 2, device 122 can illustratively cause lateral motion of a boundary in its segment of the path, as suggested by bidirectional arrows 124. Line 126 shows that device 122 can receive control signals from displacement control circuitry (not shown). Component 120 could also include trigger detecting circuitry (not shown), and the displacement control circuitry could respond to the trigger detecting circuitry by initiating operation of device 122, either in a steady state or time-varying manner; as noted above, however, trigger detection is not required for exemplary implementations described herein except as otherwise noted. Examples of how device 122 could be implemented are described below in relation to specific implementations.

If arrangement 100 in FIG. 3 includes device 122 or another device that receives control signals, it would be an example of displacement circuitry, i.e., circuitry that provides or responds to control signals by causing displacement. In general, displacement circuitry could be used together with any appropriate type of sensor, including various photosensors and impedance-based sensors as mentioned above. Another type of sensor that can include displacement circuitry is an "encoder/sensor", which may sometimes be referred to as an "encoding/sensing component" or an "encoding/sensing arrangement". An encoder/sensor operates to provide encoded sensing results, meaning that the encoder/sensor performs operations that encode information in the sensing results. The encoded information can result from relative motion produced in ways described herein, and can also result from other operations within or features of the encoder/sensor. An "encoding/sensing region", by analogy to a sensing region as defined above, is a region relative to an encoder/sensor such that the encoder/sensor can obtain sensing results from objects in the encoding/sensing region.

Figure 4:
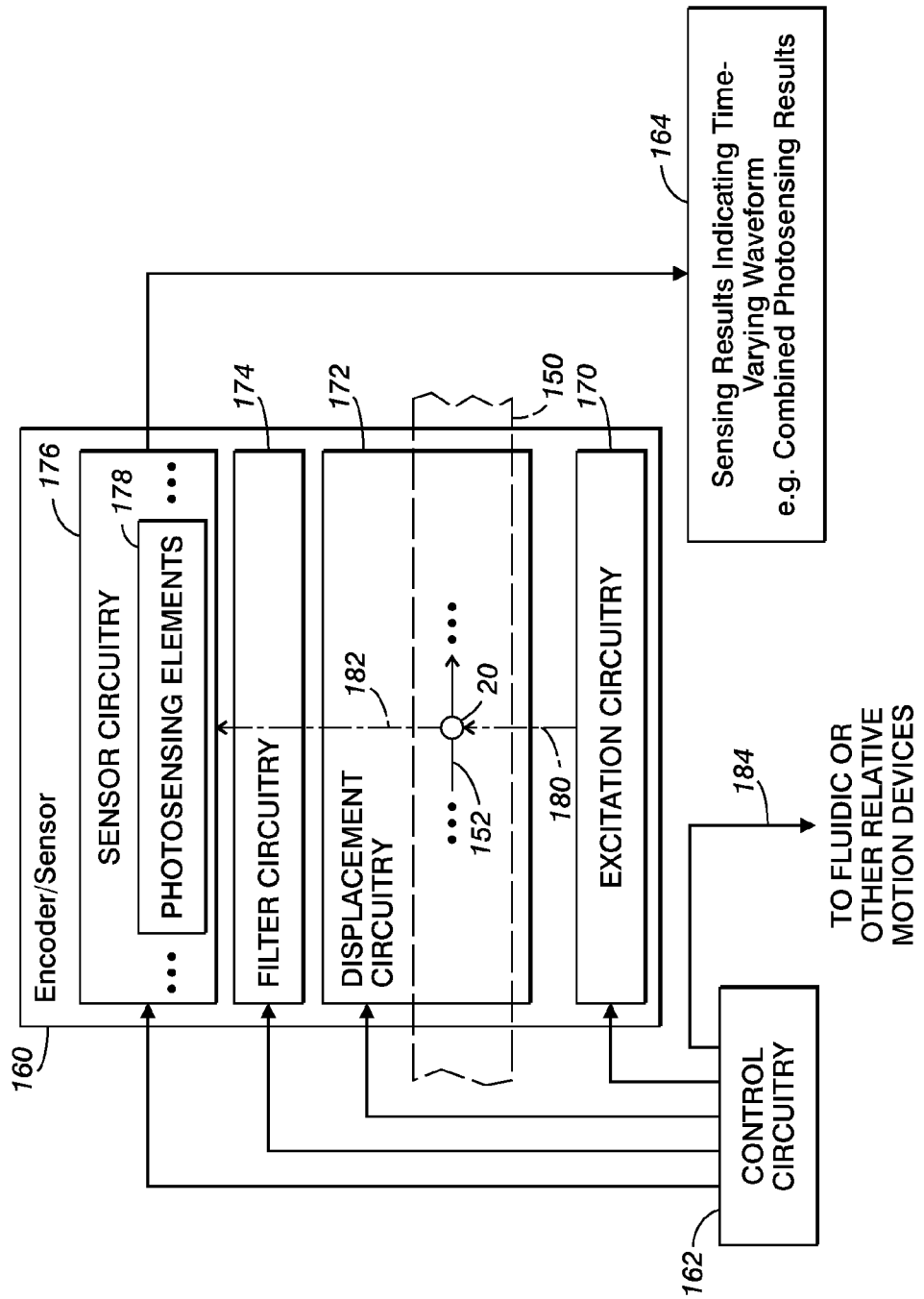
FIG. 4 is a schematic diagram showing features of implementations of sensors that can perform encoding and sensing.

FIG. 4 illustrates general features that can be included in encoder/sensors that perform photosensing of emanating light. Emanating light that includes information about an object's relative motion within an encoding/sensing region or other sensing region is sometimes referred to herein as "motion-affected" light, as including "motion-dependent information", or as having "motion-dependent encoding". For example, light emanating from an object carried in fluid, such as liquid, gas, or aerosol, could be motion-affected light as a result of one or more of an excitation pattern, nonuniform relative motion, a filtering pattern, or a sensing pattern. Similarly, light emanating from an object supported by a support structure could be motion-affected light as a result of one or more of these causes.

In FIG. 4, dashed boundary 150 represents a channel or other region in which objects can have relative motion caused by fluidic or other relative motion devices (not shown). Object 20 is one of a number of distinguishable objects that have relative motion within the region in a direction indicated by arrow 152. The path of object 20 includes a segment in which it is in an encoding/sensing region relative to encoder/sensor 160. During relative motion of object 20 within the encoding/sensing region, control signals from control circuitry 162 cause encoding of information in emanating light.

Control circuitry 162 provides control signals that cause one or both of encoder/sensor 160 and the relative motion devices to operate so that encoder/sensor 160 provides encoded sensing results indicating at least one time-varying waveform with information resulting from relative motion of object 20 within the encoding/sensing region, as shown in box 164.

Encoder/sensor 160 could be implemented in many different ways to provide encoded sensing results. FIG. 4 illustrates several different types of circuitry that it could include, though encoder/sensor 160 could also be implemented with any appropriate subset of the types of circuitry shown.

In implementations with all types of circuitry as shown, excitation circuitry 170 can be controlled to provide excitation; displacement circuitry 172 (and possibly also relative motion devices) can be controlled to provide relative displacement of object 20 within the encoding/sensing region; filter circuitry 174 can be controlled to perform filtering, such as on emanating light; and sensor circuitry 176 can be controlled to perform sensing. More specifically, sensor circuitry 176 can include photosensing elements 178, such as in a longitudinal sequence of discrete photosensing elements or a longitudinal sequence of sets of cells in a photosensing array; discrete photosensing elements or sets of cells on ICs with photosensing arrays could have different extents, different colors, or different intensities. A "longitudinal sequence" of photosensing elements or other sensing elements, as used herein, is a sequence that extends in a longitudinal direction as defined above; for example, interactions occurring in each of a sequence of segments of an object's path could be sensed by a respective sensing element in a longitudinal sequence.

In an example suggested by arrows 180 and 182, excitation circuitry 170 provides excitation light represented by arrow 180 and, in response, object 20 provides emanating light represented by arrow 182, which is filtered in response to filter circuitry 174 and sensed by photosensing elements 178. The emanating light could result, for example, from fluorescence of a dye or other "tag" attached to object 20 or from native fluorescence or autofluorescence of object 20 itself, e.g. due to ultraviolet light or other excitation of intrinsic cell material or other material in object 20; except as otherwise noted, however, implementations described herein can additionally or alternatively employ chemofluorescence, biofluorescence, absorption, scattering, or other phenomena that do not require concurrent excitation. More generally, excitation could take any appropriate form and is not limited to illumination, and excitation and emanation need not be concurrent or otherwise coincident, but could have any appropriate relationship in space and time. Some examples of excitation are described in copending U.S. patent application Ser. No. 12/023,436, entitled "Providing Time Variation in Emanating Light" and incorporated herein by reference in its entirety.

Excitation circuitry 170 could be implemented to provide a pattern of excitation within the encoding/sensing region. Filter circuitry 174 could similarly be implemented to provide a filtering pattern that receives light emanating from the encoding/sensing region, and sensor circuitry 176 could be implemented to provide a pattern with which interactions occur with objects in the encoding/sensing regions. In each of these cases, the circuitry could also include motion devices or other devices that respond to control signals by causing relative motion between objects in the encoding/sensing region and the pattern, and this relative motion could be nonuniform such as in one of the ways described herein, so that the objects have nonuniform relative motion.

On the other hand, encoder/sensor 160 may not include all types of circuitry shown in FIG. 4 in other implementations. For example, in some exemplary implementations, sensor circuitry 176 includes only an impedance-based sensing device with electrodes, Hall effect sensors, inductors, or other components in an appropriate pattern to provide encoded sensing results when interacting with an object. In such implementations, operations of excitation circuitry 170 and filter circuitry 174 would ordinarily not affect sensing results, and displacement circuitry 172 might also be ineffective in encoding information. In such implementations, one way to encode sensing results with information about an object's relative motion is to provide control signals through line 184 to fluidic or other relative motion devices, so that the relative motion itself varies in a way that encodes information. Another approach in such implementations and in certain other implementations is to operate processing circuitry to obtain data from the sensing results; this approach may be appropriate in general where the sensing results are available for sampling and analog-to-digital conversion continuously or almost continuously, making it possible for the processing circuitry to obtain data indicating a time-varying waveform indicating information resulting from the relative motion.

As a result of the controlled operation of one or both of encoder/sensor 160 and relative motion devices (not shown), sensor circuitry 176 provides sensing results indicating one or more time-varying waveforms with information resulting from relative motion of object 20 within the encoding/sensing region, as shown in box 164. More specifically, if photosensing elements 178 include a longitudinal sequence, photosensing results from the sequence could be combined to provide sensing results indicating a time-varying waveform with information resulting from the relative motion.

Figure 5:
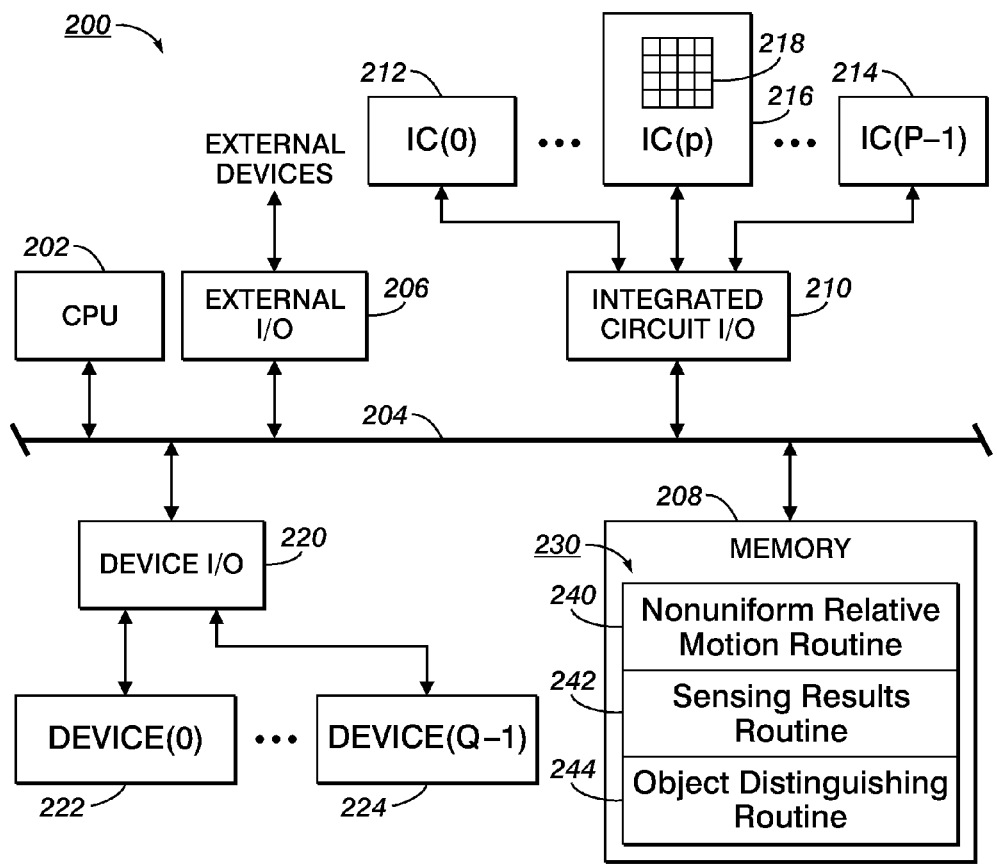
FIG. 5 is a schematic block diagram of a system in which components, such as in any of FIGS. 1-4, can be implemented.

FIG. 5 illustrates system 200, an exemplary system that could implement components as in system 10 in FIG. 1. Although system 200 illustratively includes central processing unit (CPU) 202 connected to various components through bus 204, a wide variety of other architectures could be employed, including any appropriate combination of hardware and software, as well as specialized hardware components such as application specific integrated circuits (ASICs) for one or more of the illustrated components or in place of a software component executed by CPU 202. Furthermore, CPU 202 could be the CPU component of any suitable machine such as a laptop or desktop computer, or could be a specialized computer for system 200, and CPU 202 and other digital components as shown could be replaced by other specialized circuitry, such as an analog signal processor; in a relatively simple application, CPU 202 could be implemented with a single digital signal processor or a CPU of a laptop or other personal computer receiving time-varying signals. On the other hand, in some applications, it may prove advantageous to implement all signal processing with analog circuitry, including operations that compare time-varying waveforms and that obtain their derivatives or other related waveforms, making it possible to replace substantially all the digital components as shown if appropriate.

System 200 also includes external input/output (I/O) component 206 and memory 208, both connected to bus 204. External I/O 206 permits CPU 202 to communicate with devices outside of system 200.

Figure 6:
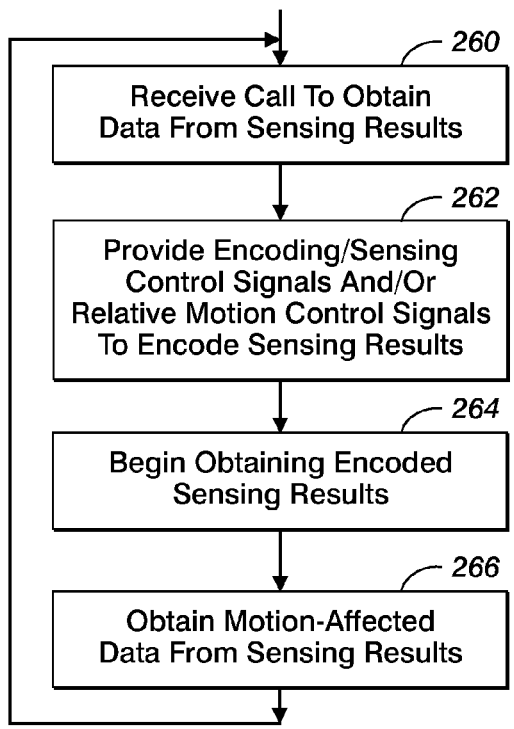
FIG. 6 is a flow chart showing general operations in an implementation of a nonuniform relative motion routine as in FIG. 5.

Additional components connected to bus 204 are within or connected to system 200. In the illustrated implementation of system 200, IC I/O 210 is a component that permits CPU 202 to communicate with ICs such as photosensing ICs; M ICs are illustrated in FIG. 6 by a series extending from IC(0) 212 to IC (P-1) 214. ICs 212 through 214 illustratively include IC(p) 216 with a photosensor array 218, which includes photosensing cells. Similarly, device I/O 220 is a component permitting CPU 202 to communicate with various devices in system 200, such as sensing and control devices; Q devices in system 200 are represented in FIG. 5 by device (0) 222 through device (Q-1) 224. In addition to excitation circuitry, displacement circuitry, and filter circuitry as described above in relation to FIG. 2, devices 222 through 224 can include relative motion devices, whether causing fluidic, scanned, rotating, or other relative motion or displacement; for example, devices 222 through 224 could include fluidic devices such as pumps, metering electrodes, smart gates, and other devices for gating and bifurcating, valves, flow or pressure sensors, and so forth. Such fluidic devices could be implemented in various ways; smart gates, for example, could be implemented with MEMS style microgates or by using electromagnetic forces, which are effective because most particles are charged such that an electric field can be used to direct them as desired in a channel.

Memory 208 illustratively includes program memory 230, although instructions for execution by CPU 202 could be provided in various other forms of software or hardware, on or off of CPU 202. The routines stored in program memory 230 illustratively include nonuniform relative motion routine 240; sensing results routine 242; and object distinguishing routine 244. In addition, program memory 230 can also store a number of subroutines (not shown) that CPU 202 can call in executing routines 240, 242, and 244.

CPU 202 executes nonuniform relative motion routine 240 to operate components of system 200 so that they cause nonuniform relative motion in one or more sensing regions, such as encoding/sensing regions in an implementation along lines described in relation to FIG. 4. In doing so, routine 240 can receive input signals from and provide output signals to devices 222 through 224. For example, to cause appropriate nonuniform relative motion of objects in a fluidic implementation, CPU 202 can receive signals from sensors, perform computations to determine what fluidic and displacement operations are necessary, and then provide signals to activate pumps, metering electrodes, gates, valves, and motion devices or other displacement devices to cause appropriate nonuniform relative motion between objects and other components of system 200. Exemplary implementations described below illustrate several examples of how routine 240 could be implemented.

CPU 202 executes sensing results routine 242 to operate components of system 200 to obtain sensing results and/or data that indicate time-varying waveforms with information resulting from nonuniform relative motion and, if appropriate, from other causes of encoding. In order to do so in an implementation in which objects emanate light, CPU 202 can, for example, perform computations to determine what control signals to provide to excitation components, filter components, sensing components, or other components or devices in order to perform appropriate encoding in emanating light in addition to encoding that results from nonuniform relative motion caused by execution of routine 240.

In one possible application of system 200, CPU 202 also executes object distinguishing routine 244, such as to obtain data indicating an object's type or other characteristic or, in some applications, to control an operation that selects objects, rejects objects, obtains further information about objects, and so forth. An example of how object distinguishing routine 244 could be implemented is described, for example, in co-pending U.S. patent application Ser. No. 12/022,485, entitled "Obtaining Information from Time Variation of Sensing Results" and incorporated herein by reference in its entirety. Techniques as described herein could be used, however, in various other applications that gather various types of information resulting from relative motion of objects within sensing regions.

Several examples of techniques that can be performed by sensing results routine 242 are described below in relation to exemplary implementations. FIG. 6 illustrates general operations that can be performed by CPU 202 in executing sensing results routine 242. In some implementations, a suitable subset of the operations illustrated in FIG. 6 might be performed, and it might also be possible to perform similar operations without a separate CPU or other processor.

The operations in FIG. 6 begin in box 260, in which CPU 202 receives or otherwise obtains a call to obtain data from sensing results encoded with information from nonuniform relative motion caused by routine 240. In response, CPU 202 could prepare to obtain sensing results, such as by providing readout control signals to one or more of ICs 212 through 214 or by monitoring output from impedance-based sensors or other sensors that provide sensed quantities continuously, whether in analog or digital form.

In reading out photosensed quantities, for example, CPU 202 can perform pre-sensing readout, obtain object information and sensing periods, perform sensing readout with sensing periods and analog adjustment, digitally adjust sensing results and store quantities for an object, and combine the quantities for an object to produce its characteristic data. CPU 202 could, for example, call a subroutine implemented as described in U.S. Pat. No. 7,358,476, entitled "Sensing Photons from Objects in Channels", and 2007/0146704, entitled "Sensing Photon Energies Emanating from Channels or Moving Objects", each of which is incorporated herein by reference in its entirety. Such a subroutine can be implemented for single objects moving past arrays or for spaced multiple objects moving past arrays, provided spacings between objects are sufficient to avoid having more than one object in a sensing region or other kinds of interference. Also, such a subroutine can follow a general strategy of performing a series of readout operations, after which information for an object is combined and its characteristic data is provided, although it would also be possible to provide the information from each readout operation immediately.

In any case, CPU 202 can then make certain modifications in its sensing operations in order to obtain motion-affected sensing results and/or data. One type of modification is illustrated by the operation in box 262, in which CPU 202 provides control signals that cause encoding/sensing and/or relative motion such that the sensing results are encoded to indicate time-varying waveforms with information resulting from nonuniform relative motion. After the operation in box 262, CPU 202 begins to obtain encoded sensing results, in accordance with the control signals provided in box 262, as illustrated by box 264.

In the implementation in FIG. 6, operations of CPU 202 in box 266 then use encoded sensing results obtained by operations in box 264 to obtain motion-affected data. CPU 202 can, for example, implement the operation in box 266 by obtaining data from the encoded sensing results in a way that preserves information resulting from relative motion. In other implementations, CPU 202 could obtain motion-affected data in other ways that do not require control signals as in box 262, such as with impedance-based sensing; in these cases, the sensing results might, for example, be inherently encoded without the need for control signals as in box 262, so that CPU 202 can obtain data in a way that preserves the inherently encoded information resulting from nonuniform relative motion without providing control signals as such.

After the operations in FIG. 6 have obtained motion-affected sensing results and/or data, CPU 202 can return and await another call in box 260, as suggested by the arrow from box 266 returning to box 260. In more sophisticated implementations, CPU 202 could perform operations similar to those in FIG. 6 concurrently for several different sensors.

Figure 7:
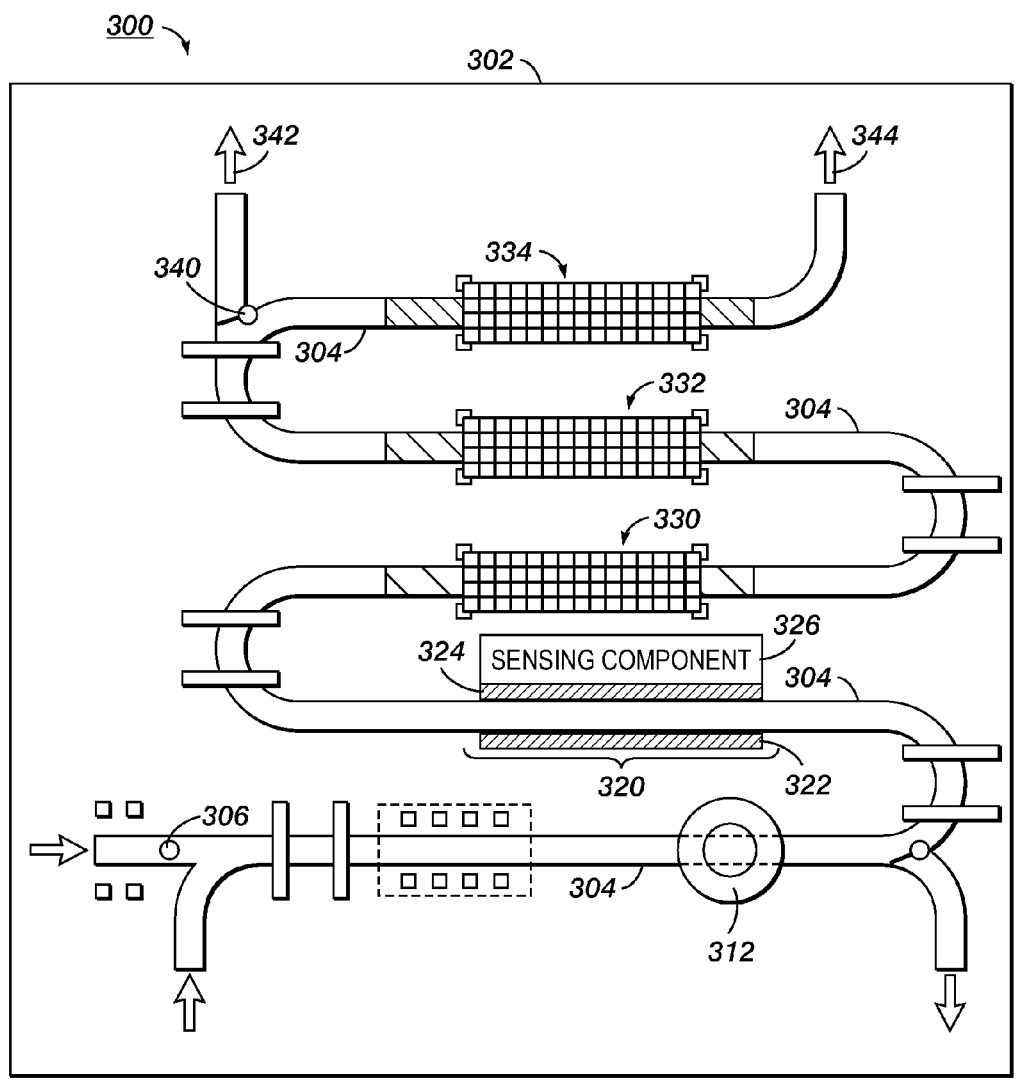
FIG. 7 is a schematic diagram of an analyzer in a fluidic structure, where the analyzer can include a system that can be implemented as in FIGS. 5 and 6.

FIG. 7 illustrates an application of a system as in FIGS. 5 and 6 in analyzer 300 on support structure 302, a fluidic structure. Defined in support structure 302 is serpentine channel 304 through which object 306 can have relative motion, carried by fluid such as liquid, gas, or aerosol or moved in some other appropriate way. Object 306 can, for example, be a biological cell or another object of any of the types mentioned above.

The manner in which object 306 enters channel 304 and is carried by fluid can be the same as described in U.S. Pat. No. 7,358,476, entitled "Sensing Photons from Objects in Channels", and 2007/0146704, entitled "Sensing Photon Energies Emanating from Channels or Moving Objects", each of which is incorporated herein by reference in its entirety. As explained there, object 306 can be carried through channel 304 by operation of propulsion components and can be purged or otherwise caused to exit, together with fluid that is carrying it, from one of several outlets, such as through toggling of valves. While in channel 304, object 306 can have relative motion within interaction regions relative to a series of object interaction components, each of which can obtain information about object 306.

The first two interaction components after object 306 enters channel 304 are illustratively Coulter counter 310, an electrically based particle size detector, and Mie scatter sensor 312, also a particle size detector. Information about size of object 306 from Coulter counter 310 and Mie scatter sensor 312 can be used in obtaining information about its other characteristics. Various other techniques could also be used to obtain particle size information, including techniques that use chirped filter patterns, random filter patterns with small feature size, staircase periodic filter patterns, and so forth, and such techniques could make it unnecessary to use specialized components to determine particle size.

The next interaction component along channel 304 is object interaction component 320, shown schematically in a cross-sectional view along an axis similar to the x OR t axis in FIG. 3, although it would typically be implemented instead with components above and below channel 304, similarly to other object interaction components described below. The schematic illustration of component 320 illustratively includes excitation/displacement component 322, filter component 324, and sensing component 326, all of which might be implemented in a variety of ways, including some of those described above and below; one or more of components 322, 324, and 326 could be omitted or replaced in specific implementations. In addition, component 320 could include a displacement control arrangement with shaped boundaries and/or a motion device or other displacement component (not shown) implemented in one of the ways described above or below.

After passing through component 320, object 306 could be characterized without obtaining further information, or, as in the illustrated implementation, object 306 can continue through subsequent object interaction components, illustratively including components 330, 332, and 334. These could, for example, include first and second fluorescence sensing components and a Raman scatter sensing component. Information obtained from any combination of the object interaction components can be used to distinguish between types of objects, such as different types of biological cells, or to distinguish objects from environment or background. Based on such a distinction, valve 340 at a bifurcation junction can be toggled between two positions, with object 306 exiting as indicating by arrow 342 if valve 340 is in one position and exiting as indicated by arrow 344 if valve 340 is in another position.

The fluidic implementation in FIG. 7 is merely illustrative of a wide variety of implementations of the techniques described herein. For example, any appropriate fluidic or nonfluidic techniques could be used with a wide variety of different types of objects and various types of nonuniform relative motion to obtain various types of motion-affected sensing results or data.

FIGS. 8-11 illustrate examples in which laminar flow can produce nonuniform displacement or other nonuniform relative motion, as a result of shaped boundaries and/or motion devices in channel motion mechanisms as described above in general terms in relation to FIG. 3. Implementations as in FIGS. 8-11 could be included in object interaction component 320 in FIG. 7 or in other encoding/sensing components.

Figure 8:
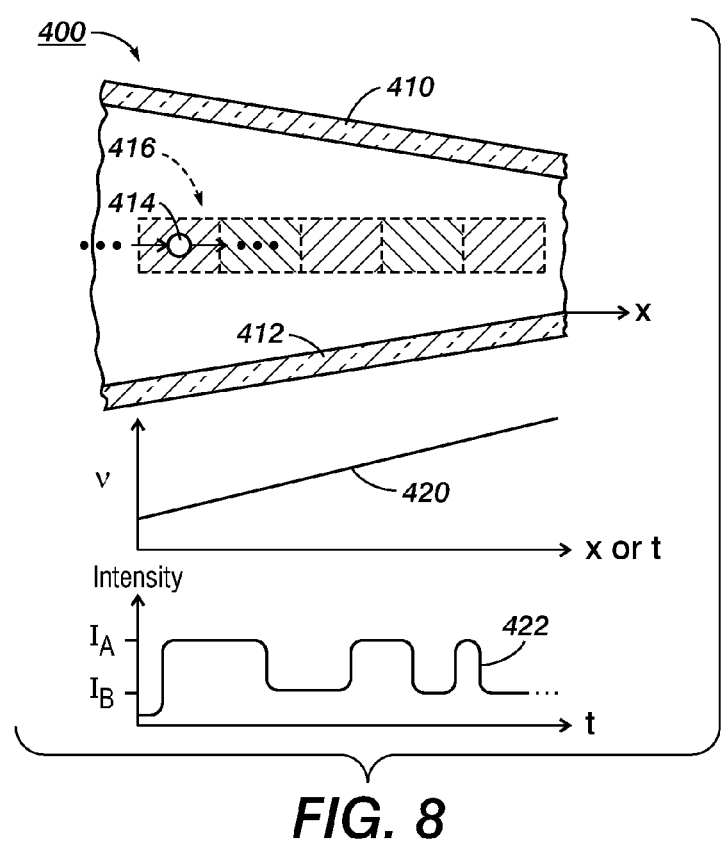
FIG. 8 is a partially schematic cross-sectional view of a fluidic component that could be implemented in an analyzer as in FIG. 7, together with graphs showing velocity and intensity as functions of time.

FIG. 8 shows a cross section of component 400, taken along a line similar to that of object interaction component 320 in FIG. 7. Component 400 provides an example of shaped boundaries, with wall-like parts 410 and 412 having linearly decreasing distance between them. As a result, as object 414 passes through interdigitated two-color pattern 416 in response to longitudinal flow of fluid carrying it, its velocity increases linearly as indicated by curve 420, either as a function of position or of time. Therefore, rather than a periodic time-varying signal as would be provided if object 414 had uniform relative motion, the resulting time-varying signal is chirped, meaning that itsperiods decrease linearly due to chirp-varying relative motion of object 414 resulting from change in flow speed of fluid in the channel as channel dimensions change.

Pattern 416 could be provided in any appropriate way. For example, its regions could be excitation regions as described in co-pending U.S. patent application Ser. No. 12/023,436, entitled "Producing Time Variation in Emanating Light" and incorporated herein by reference; filter elements as described in co-pending U.S. patent application Ser. No. 12/024,490, entitled "Transmitting/Reflecting Emanating Light with Time Variation" and incorporated herein by reference; or other types of regions such as discrete photosensing elements or parts of a photosensing array. If implemented as filter elements, photosensing elements, or parts of a photosensing array, the regions could be surrounded as appropriate by blocking regions (not shown); blocking regions and other techniques used in sensing arrangements are described in more detail in co-pending U.S. patent application Ser. No. 12/337,737, entitled "Obtaining Sensing Results Indicating Time-Variation" and incorporated herein by reference in its entirety.

Curve 422 illustrates the resulting sensing results, i.e. a chirped signal that has alternating intensities I(A) and I(B). As can be seen, the duration of the signal during each successive region of pattern 416 is shorter than the preceding region, resulting in the chirped pattern. For the sake of illustration, the linear decrease in transition time is exaggerated in curve 422 in comparison to the narrowing of the channel.

The technique in FIG. 8 is only one of a variety of ways of causing chirp-varying relative motion, and various other techniques could be used. Also, more complex flow speed distributions could be obtained by modifying the channel walls in other ways or by providing devices that change the flow speed or flow pattern within the channel, any of which would produce more complex nonuniform relative motion. In addition, multicolor interdigitated interference patterns could be used, or excitation patterns could be created with holographic techniques.

Figure 9:
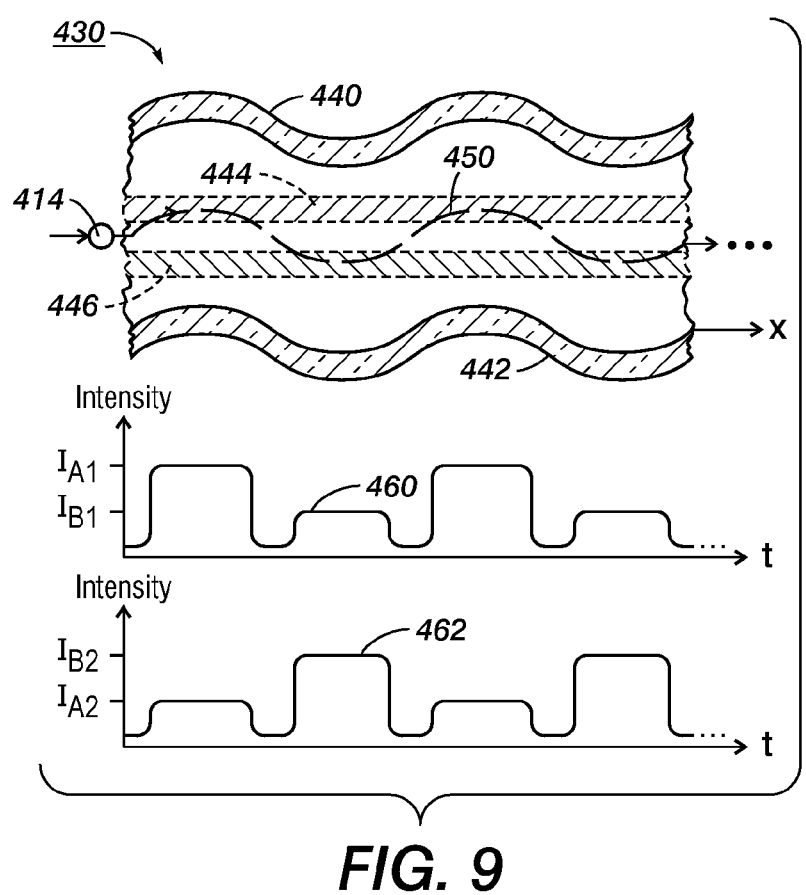
FIG. 9 is a partially schematic cross-sectional view of another fluidic component that could be implemented in an analyzer as in FIG. 7, together with graphs showing intensity as functions of time.

The cross section of component 430 in FIG. 9 illustrates, on the other hand, how relatively simple nonuniform relative motion could be caused using more complicated techniques. In general, such techniques assume that geometry of a channel directs flow of object 414 in a defined manner, such as with periodically varying, chirp-varying, or randomly varying relative motion, through a sequence of excitation regions. If, for example, laminar flow is maintained through an excitation pattern, as described above, excitation regions would remain undisturbed by channel walls, and can therefore remain homogeneous. More generally, such techniques allow redirection of particle flow through a simpler patterned environment, and may be advantageous in cases where it is easier to redirect particle flow to obtain sensing results with desired time-variation than it would be to produce a patterned environment to produce the same time variation; for example, it might be easier to change channel wall shapes than to produce a desired excitation source. In other cases, on the other hand, it might be advantageous to obtain more abrupt or rapid signal transitions with a well-defined patterned environment. In addition to the techniques described below, which involve shaping or moving walls, an object's nonuniform relative motion within a channel could also be caused by other techniques; an electrically charged object such as a particle, for example, could be redirected by electrical field variations. In general, however, the Reynolds numbers in typical microfluidic and nanofluidic implementations are so small that laminar flow conditions are, as a practical matter, always present.

In the example in FIG. 9, wall-like parts 440 and 442 are parallel, but each of them is shaped like a sinusoidal wave, resulting in a sinusoidal flow pattern in the channel between them that causes periodically varying relative motion along a sinusoidal path. Regions 444 and 446 are homogeneous of two different colors or gray levels, illustratively labeled "A" and "B". For example, regions 444 and 446 could be stripe-like excitation regions as described in co-pending U.S. patent application Ser. No. 12/023,436, entitled "Producing Time Variation in Emanating Light" and incorporated herein by reference; stripe-like filter elements as described in co-pending U.S. patent application Ser. No. 12/024,490, entitled "Transmitting/Reflecting Emanating Light with Time Variation" and incorporated herein by reference; or other types of regions such as discrete photosensing elements or parts of a photosensing array. If implemented as filter elements, photosensing elements, or parts of a photosensing array, the regions could be separated and surrounded as appropriate by blocking regions (not shown).

As object 414 follows sinusoidal path 450, it moves back and forth between regions 444 and 446, passing through a small gap between them twice during each period. Curves 460 and 462 illustrate exemplary sensing results, i.e. time-varying signals that could result from an object traveling along path 450. Curve 460 illustrates an example of an object of a type that responds strongly to or emanates strongly at color or gray level A but responds only weakly to or emanates only weakly at color or gray level B, while curve 462 illustrates an example of an object of a type that responds strongly to or emanates strongly at color or gray level B and responds weakly to or emanates weakly at color or gray level A. As a result, the curves are somewhat complementary, although each curve goes to approximately 0 while path 450 is crossing the gap between regions 444 and 446.

Figure 10:
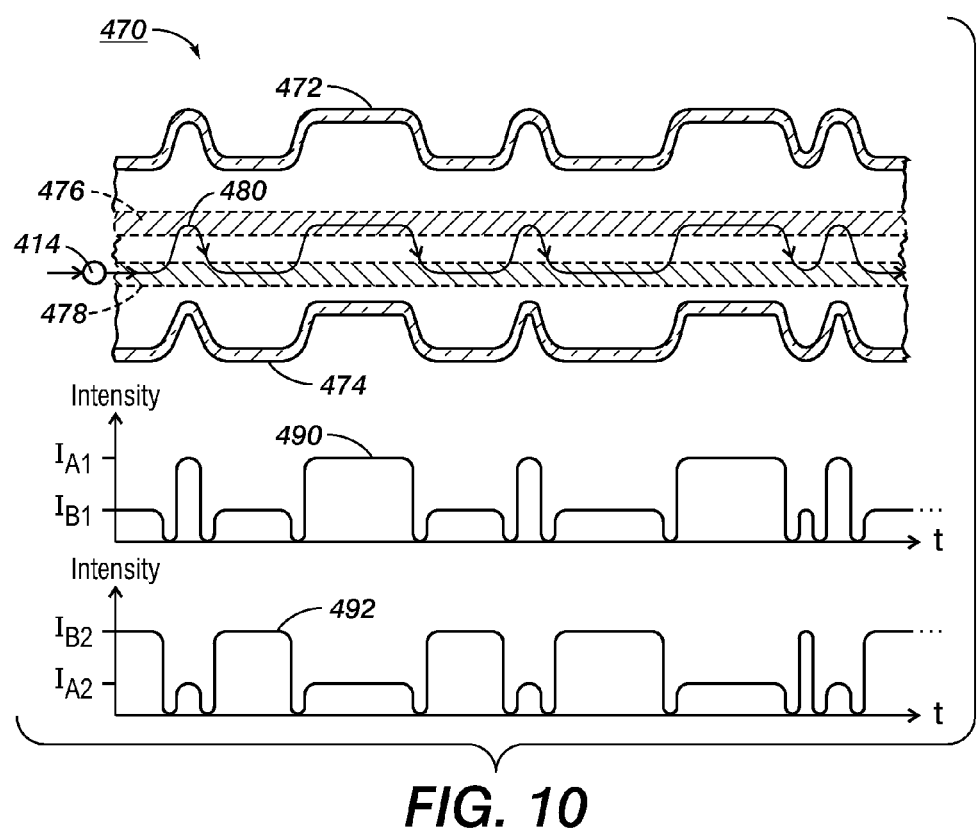
FIG. 10 is a partially schematic cross-sectional view of another fluidic component that could be implemented in an analyzer.

The cross section of component 470 in FIG. 10 illustrates another way in which relatively simple nonuniform relative motion could be caused using more complicated techniques, similar in ways to the exemplary implementation of FIG. 9. In the example in FIG. 10, wall-like parts 472 and 474 have inner surfaces that are parallel, but each of them is shaped with random variations, resulting in a randomly varying flow pattern in the channel between them that causes randomly varying relative motion along a path; the variety of possible random variations allows a broad scope of arbitrary sequences, although design limitations would limit minimum feature size and the abruptness with which changes could be made. Regions 476 and 478 are homogeneous of two different colors or gray levels, illustratively labeled "A" and "B", as described above in relation to FIG. 9.

As object 414 follows randomly varying path 480, it moves back and forth between regions 476 and 478, passing through a small gap between them. Curves 490 and 492 illustrate exemplary sensing results, i.e. time-varying signals that could result from an object traveling along path 480. Curve 490 illustrates an example of an object of a type that responds strongly to or emanates strongly at color or gray level A but responds only weakly to or emanates only weakly at color or gray level B, while curve 492 illustrates an example of an object of a type that responds strongly to or emanates strongly at color or gray level B and responds weakly to or emanates weakly at color or gray level A. As a result, the curves are somewhat complementary, although each curve goes to approximately 0 while path 480 is crossing the gap between regions 476 and 478.

Figure 11:
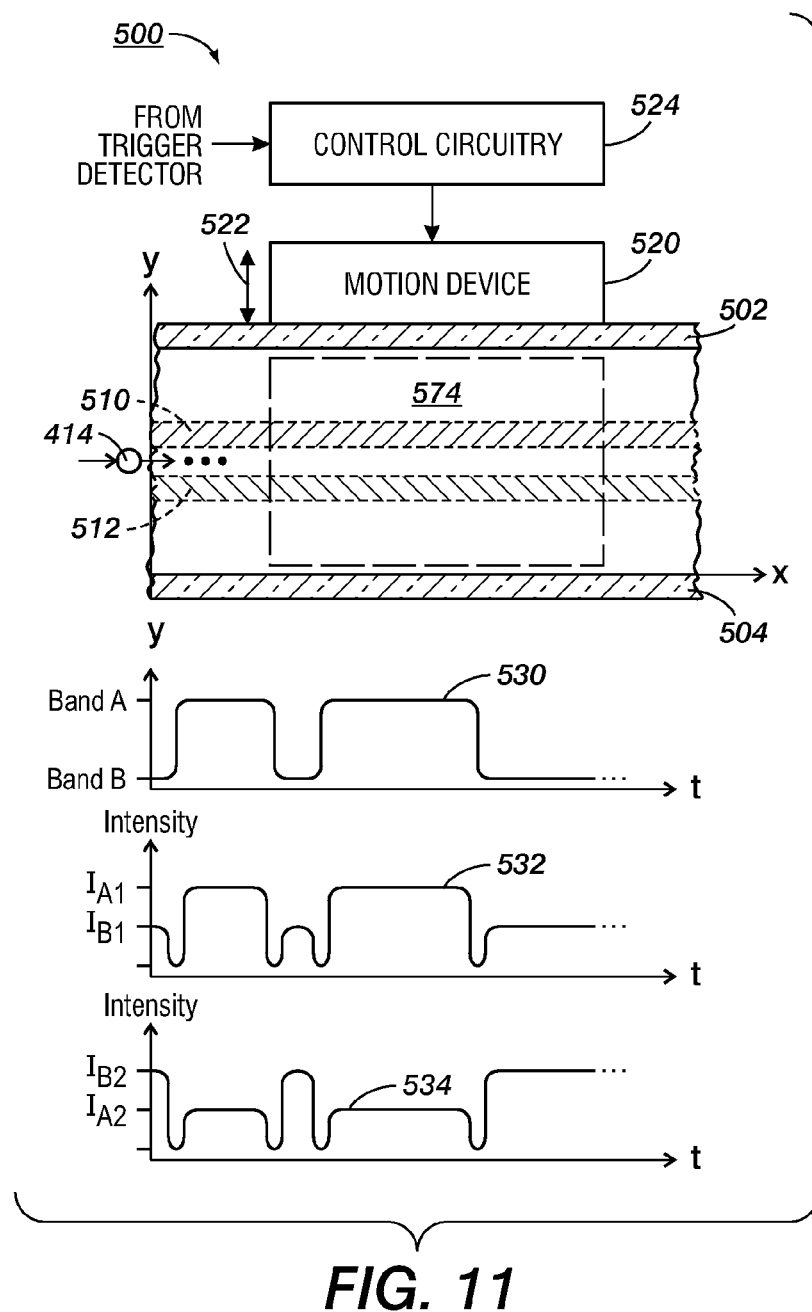
FIG. 11 is a partially schematic cross-sectional view of a component that could be implemented in a system as in FIGS. 5-7 and in which control signals are provided to a motion device to produce displacement, together with a graph showing displacement as a function of time and graphs showing sensing results as a function of time for exemplary types of objects.

FIG. 11 illustrates component 500, in which motion-affected sensing results encode information about nonuniform relative motion caused by providing control signals to a motion device or other displacement circuitry. In this exemplary implementation, wall-like parts 502 and 504 are substantially straight and parallel and without some additional cause would therefore result in uniform relative motion. Between parts 502 and 504 are longitudinal regions 510 and 512, each extending in the longitudinal direction across encoding/sensing region 514 and which could therefore be implemented in any of the ways described above for regions 444 and 446 (FIG. 9).

Motion device 520, which could be an electrically controlled device such as a solenoid or motor-driven piston, causes lateral relative motion between object 414 and regions 510 and 512, as indicated by bidirectional arrow 522. Control circuitry 524 provides signals to control operation of motion device 520, illustratively in response to trigger signals from a trigger detector (not shown). The nonuniform relative motion caused by operation of motion device 520 need not be periodic, but could have any appropriate type of speed/direction variation, resulting in sensing results that can include arbitrary time-varying signals with features indicating different types of objects. An alternative way to produce relative motion would be to move the light sources or other components that control positions of regions 510 and 512; more generally, any combination of relative motions between walls 502 and 504 on the one hand and regions 510 and 512 on the other could produce movement as indicated by bidirectional arrow 522. Furthermore, additional speed/direction variations could be produced by changing fluid flow within the channel so that the speed or other displacement of object 414 changes as a function of time relative to the other movements.

Curve 530 illustrates movement of object 414 in the y-direction between region 510, labeled "Band A", and region 512, labeled "Band B". As illustrated, object 414 spends different lengths of time in each region and can spend a random amount of time in each region, an example of randomly varying relative motion. Curves 532 and 534 illustrate exemplary sensing results, i.e. time-varying signals that could be obtained by the technique of FIG. 11 if regions 510 and 512 provide excitation, filtering, or sensing in Band A and Band B, respectively. One type of object responds more strongly to or emanates more strongly at color A in region 510, as illustrated by curve 532, while the other responds more strongly to or emanates more strongly at color B in region 512, as illustrated by curve 534. As each object's relative motion takes it between regions 510 and 512, it passes through the gap between the regions, resulting in a brief interruption of excitation or sensing, so that each curve goes briefly to 0. In curve 532, the intensity in region 510 is I(A1), while the intensity in region 512 is I(B1), a lower value. Conversely, curve 534 illustrates that the intensity is higher in region 512, at intensity I(B2), and lower in region 510, at intensity I(A2). The two curves are, in general, complementary, except for times when they are passing through the gap between regions 510 and 512; object 414 can be moved instantaneously between Band A and Band B, moving very quickly across the gap between regions 510 and 512, so that the times in which it is passing through the gap are very brief.

Figure 12:
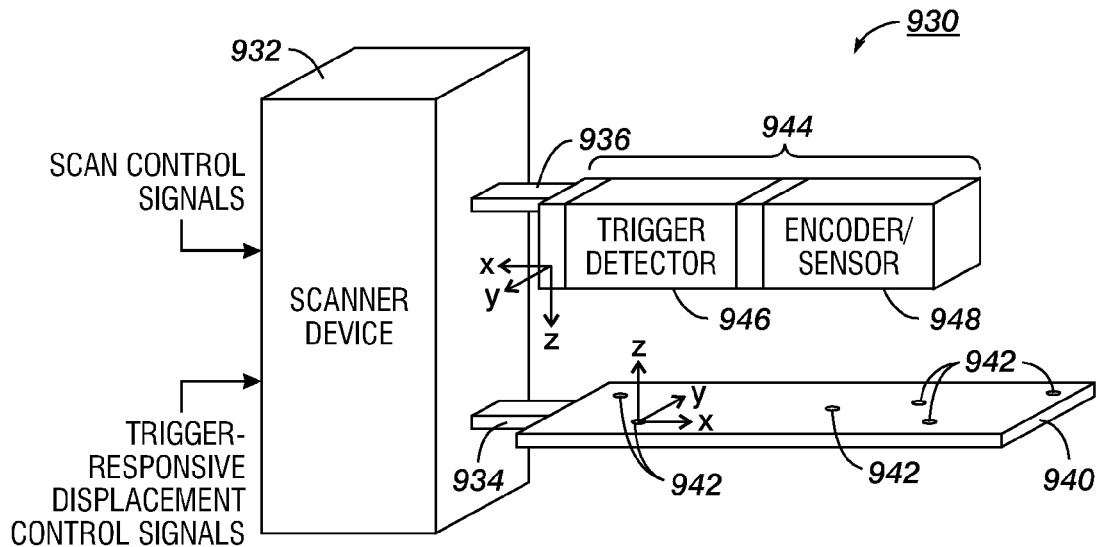
FIG. 12 is a partially schematic perspective view of a system that can be implemented as in FIG. 5 and that includes a scanner device.
Figure 13:
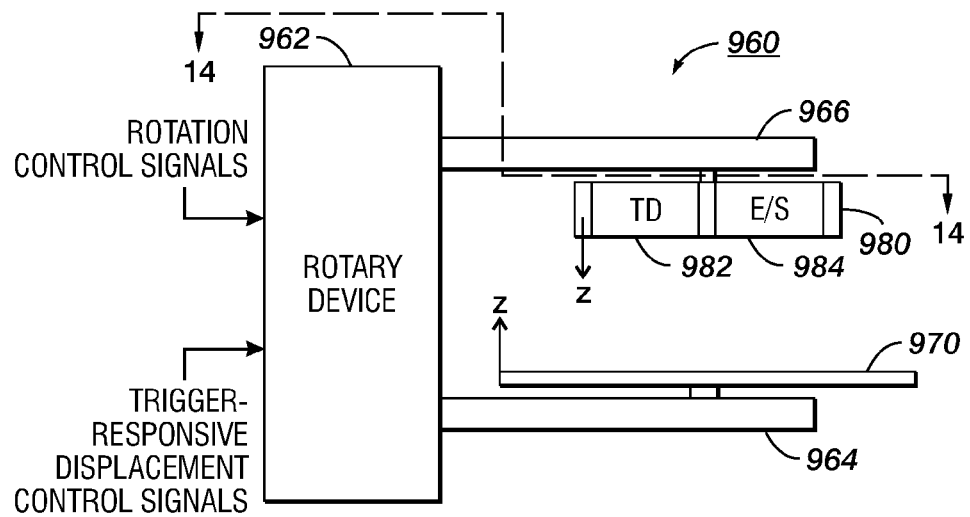
FIG. 13 is a partially schematic side view of a system that can be implemented as in FIG. 5 and that includes a rotary device.
Figure 14:
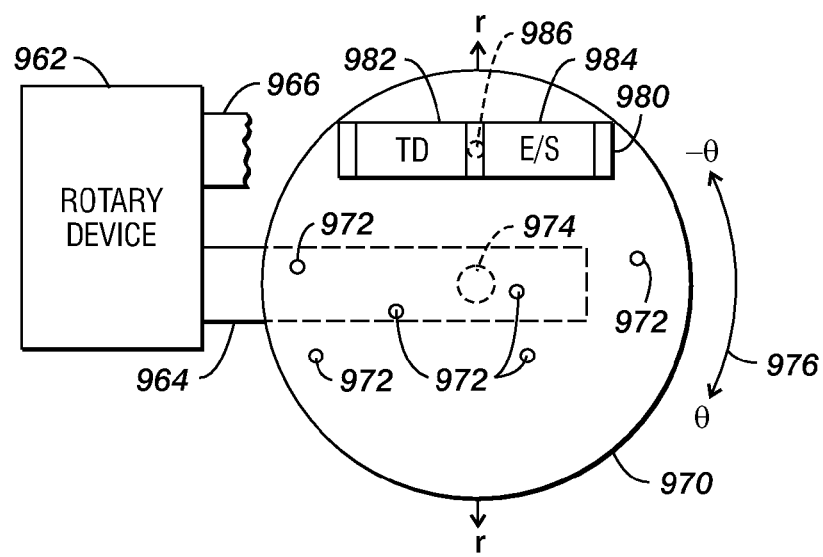
FIG. 14 is a partially schematic cross-sectional top view, taken along the line 14-14 in FIG. 12.

As indicated above, nonuniform relative motion techniques are not limited to implementations in which relative motion in fluidic structures is caused by fluidic devices, but could be used with other types of relative motion, including relative motion caused by non-fluidic devices and in non-fluidic structures. FIGS. 12-14 illustrate examples in which non-fluidic devices produce nonuniform relative motion, such as modulated relative motion as described above. In general, the techniques in FIGS. 12-14 can be implemented in various ways, including, in some cases, certain features shown and described in U.S. Pat. No. 7,420,677, incorporated herein by reference in its entirety.

The implementations illustrated in FIGS. 12-14 allow nonuniform relative motion between two components, one of which includes a support structure on which one or more objects are supported and the other of which includes an object interaction unit with a trigger detector and an encoder/sensor. In the illustrated examples, both of these components can be moved by a device in response to control signals, but the techniques described could be implemented with systems in which one of the components is stationary and only the other one is moved by the device in response to control signals. Furthermore, the illustrated implementations could be operated in this manner simply by holding one component stationary, although this would reduce the possible range of relative motion in some cases.

In contrast to an encoder/sensor, a "trigger detector", which may sometimes be referred to as a "trigger detecting component" or a "trigger detecting device", is a sensor that responds to a detected condition or event by providing a signal indicating the condition or event's detection, typically referred to herein as a "trigger signal". For example, a trigger detector could provide a trigger signal when it detects a distinguishable object in a particular region. A trigger detector can be a discrete component or device, or it could be provided by operations that read out a trigger part of a photosensing array or in another appropriate way. Features of implementations with trigger detectors are described in greater detail in co-pending U.S. patent application Ser. No. 12/337,771, entitled "Obtaining Sensing Results and/or Data in Response to Object Detection" and incorporated by reference herein in its entirety; as noted above, however, use of trigger detectors are not in general required herein, and implementations similar to those in FIGS. 12-14 could omit trigger detectors.

In the implementations in FIGS. 12-14, the support structure could take any suitable form, such as a slide on which objects are positioned, a bed or disk on which objects are positioned, or even a fluidic device with one or more channels within which objects are immobilized, such as by binding to particles within a gel, or are moving slowly relative to the nonuniform relative motion caused by device operations; the support structure could also include, for example, a pair of slides with objects positioned between them such as in sputum or other liquid, a capillary tube containing objects, a biochip, an array of wells, a well plate, and so forth, any of which could be positioned on another part of the support structure such as a scanner bed or rotating disk. The object interaction units could similarly be implemented in a wide variety of ways with various types of trigger detectors and encoder/sensors positioned relative to each other in various ways or, where appropriate, without a trigger detector or with another type of sensor; the detection and sensing could make use of any suitable type of interaction, including optical sensing of light emanating from objects, impedance-based sensing such as with electrodes or Hall effect devices, or even possibly piezoelectric or other pressure-based sensing of acoustic signals emanating from objects. Furthermore, the encoder/sensor can include any suitable combination of circuitry, including circuitry to control, for example, excitation, filtering, and sensing; in optical implementations, an object interaction unit could include an IC with an array of photosensing cells, operated with one or more trigger parts that serve as trigger detectors and one or more pattern parts that serve as encoder/sensors.

System 930 in FIG. 12 includes scanner device 932 with support components 934 and 936. Support structure 940 is mounted on support component 934, and it supports a number of distinguishable objects 942. Object interaction unit 944 is mounted on support component 936, and it includes at least one trigger detector 946 and at least one encoder/sensor 948. As illustrated by the two complementary sets of x-, y-, and z-axes for one of objects 942 and for object interaction unit 944, any specified relative motion between support structure 940 and object interaction unit 944 can be accomplished by moving either or both of them such that the net result of their movements is the specified nonuniform relative motion. The x-axis indicates a scanning direction in which scanner device 932 can cause relative motion between object interaction unit 944 and support structure 940 such that a given object 942 can have relative motion into a trigger detection region relative to trigger detector 946, then from the trigger detection region into an encoding/sensing region relative to encoder/sensor 948, and then within the encoding/sensing region, resulting in motion-affected sensing results or data as described above. The y-axis illustrates a direction of relative motion in which the distance between support structure 940 and object interaction unit 944 can remain constant, but displacement can occur perpendicular to the scanning direction. The z-axis illustrates a direction in which support structure 940 and object interaction unit 944 can move closer to or farther away from each other.

In operation, scanner device 932 responds to scan control signals, such as from CPU 202 through device control IO 220 (FIG. 5), by moving support structure 940 and/or object interaction unit 944 to produce relative motion in the scanning direction; CPU 202 could, for example, provide the scan control signals while executing nonuniform relative motion routine 240 (FIG. 5). Then, when trigger detector 946 provides a trigger signal indicating relative motion of one of objects 942 into its trigger detection region, CPU 202 can provide trigger-responsive displacement control signals to scanner device 932, which responds with movement of one or both of support structure 940 and object control unit 944 to cause displacement while object 942 has relative motion within the encoding/sensing region of encoder/sensor 948. Displacement in any of the three directions indicated by the x-, y-, z-axes can be used to obtain motion-affected sensing results and/or data that indicate time-varying waveforms with information resulting from the relative motion to which support structures 970 and 980 are stably attached; for added precision, it might also be possible to independently displace trigger detector 982 and encoder/sensor 984, such as in the z-direction. In particular, displacement in any of the three indicated directions can include one or more modulation cycles within the encoding/sensing region, so that the scanning motion is a carrier component and the displacement includes modulation cycles.

FIGS. 13 and 14 show system 960 from a side view and from a top view with partial cross section, respectively. System 960 includes rotary device 962, a device that can produce rotating motion through one or both of support components 964 and 966; rotary device 962 might, for example, be a miniaturized device such as a MEMS or nanotechnology device. Support structure 970 is illustratively circular, supporting objects 972, but could have any appropriate shape and in other respects could be implemented similarly to support structure 940 in FIG. 12. Support structure 970, however, can rotate about axis 974 as indicated by bidirectional arrow 976. Object interaction unit 980, similarly to object interaction unit 944 in FIG. 12, includes trigger detector (TD) 982 and encoder/sensor (E/S) 984. Object interaction unit 980 can also illustratively rotate about axis 986, although that type of relative motion is not employed in the particular technique illustrated in FIGS. 13 and 14. Various additional types of motion are possible, such as independent height adjustment in the z-direction for TD 982 and E/S 984.

Three dimensions of relative motion illustrated in FIGS. 13 and 14 include a θ-direction that is a direction of rotation indicated by arrow 976 and that can be measured as an angle of rotation; an r-direction that can be measured as a distance from an axis of rotation of support structure 970 to object interaction unit 980; and a z-direction that is the same as the z-direction in FIG. 12. For example, while support structure 970 is rotating in the θ-direction, an object 972 can have relative motion into the trigger detection region of trigger detector 982, with the rotating motion being produced by rotary device 962 in response to rotation control signals, similar to the scan control signals described above in relation to FIG. 12. Then, in response to trigger-responsive displacement control signals from CPU 202 (FIG. 5) as described above, rotary device 962 can produce displacement in any of the θ-, r-, and z-directions while object 972 has relative motion within the encoding/sensing region of encoder/sensor 984. As indicated by the complementary r-axes and z-axes on support structure 970 and on object interaction unit 980, rotary device 962 can produce displacement in these two directions by moving one or both of support components 964 and 966 to which support structures 970 and 980 are stably attached; for added precision, it might also be possible to independently displace trigger detector 982 and encoder/sensor 984, such as in the z-direction. As above, the resulting displacement can provide motion-affected sensing results and/or data. In particular, the displacement can include one or more modulation cycles within the encoding/sensing region, so that the rotating motion is a carrier component and the displacement includes modulation cycles.

In the above-described implementations of scanning device 932 and rotary device 962, information is encoded as result of nonuniform relative motion caused within encoding/sensing regions in response to trigger signals, and the nonuniform relative motion illustratively includes displacement caused by trigger-responsive control signals. Encoding could instead, however, be performed without trigger-responsive displacement, such as by providing continuous nonuniform relative motion. Also, nonuniform relative motion could produce sensing results that are also encoded in response to control signals to one or more of excitation, filter, or sensing circuitry within encoder/sensors 948 and 984. Furthermore, various other modifications could be made in the above-described techniques to obtain motion-affected sensing results and/or data.

Implementations as described above in relation to FIGS. 1-14 could be advantageously applied in a wide variety of sensing applications, possibly including, for example, fluorescence- or impedance-based flow cytometry or other biodetector applications that seek a signature of a particle of unknown velocity; such biodetectors often use microfluidic channels with inhomogeneous flow profiles, causing variation in particle velocity. The techniques can be used to count or obtain ratios between fluorescing objects of different types, such as different types of tagged cells, particles, tagged DNA, and so forth. In such an application, calibration can be performed using known objects, e.g. tagged beads, with known velocities to obtain template waveforms that include deviations caused by fabrication tolerances but can then be compared with sensed waveforms to obtain information about unknown objects.

Implementations described above may be advantageous in biodetector applications that require compact, low-cost components without critical optics and with high sensing efficiency. Such applications might include point-of-care flow cytometry (such as with an integrated flow cytometer), DNA analysis, proteomics, and so forth.

Also, implementations described above could be applied in scanning of bio-chips or documents where objects have different emanation spectra, and so forth. The techniques may also be applicable in various low S/N ratio systems in which a known signal is bounced off an object traveling at an unknown velocity, such as where object velocity is on the order of signal propagation velocity, as in SONAR. The techniques may be especially advantageous where precise information about position, speed, or type of objects is sought.

Some of the implementations described above in relation to FIGS. 1-14 are examples of a system that includes a sensor and a relative motion component. The sensor, in operation, obtains sensing results from objects in a sensing region relative to the sensor. In operation, the relative motion component causes respective relative motion of each of a subset of the objects, and each object in the subset has respective relative motion within the sensing region. The relative motion component causes at least one object's relative motion within the sensing region to be nonuniform, with the nonuniform motion including at least one of periodically varying relative motion, randomly varying relative motion, chirp-varying relative motion, and modulated relative motion that completes at least one modulation cycle within the sensing region.

In specific implementations, the sensing results can include motion-encoded information resulting from the nonuniform relative motion; the sensing results can include independently encoded information resulting from encoding performed by the sensor independently of the nonuniform relative motion; and/or the sensing results can indicate at least one waveform with time variation resulting from the nonuniform relative motion. For example, the sensor can perform encoding independently of the nonuniform relative motion, and the sensing results can include independently encoded information resulting from the encoding performed by the sensor independently of the nonuniform relative motion. The sensor can, for example, include at least one of excitation circuitry that, in operation, provides time-varying excitation to objects in the sensing region; filter circuitry that, in operation, provides time-varying filtering of light emanating from objects in the sensing region; and sensor circuitry that, in operation, provides sensing results that indicate one or more waveforms with time variation resulting both from the nonuniform relative motion and from encoding performed independently of the nonuniform relative motion.

In further specific implementations, the sensor can include at least one of an excitation component that provides a pattern of excitation in the sensing region; a filter component that filters light emanating from objects in the sensing region with a filtering pattern; and a sensing component that performs sensing by interacting with objects in the sensing region with a sensing pattern, and that includes a photosensor and/or an impedance-based sensor. In general, the sensor can include a photosensor and/or an impedance-based sensor, and the sensor can obtain the sensing results so that they indicate at least one waveform with time variation resulting from the nonuniform relative motion.

In further specific implementations, the relative motion component can cause each object in the subset to have respective relative motion into the sensing region and respective relative motion out of the sensing region. The relative motion component can include at least one of a motion-varying mechanism that, in operation, causes the nonuniform relative motion by varying one or both of speed and direction of objects' relative motion within the sensing region; a fluidic motion mechanism that, in operation, controls flow of fluid carrying objects within the sensing region; a channel motion mechanism that, in operation, controls movement of a channel that includes the sensing region and through which objects are carried by fluid; a support motion mechanism that, in operation, controls movement of a structure supporting objects; a sensor motion mechanism that, in operation, controls movement of the sensor; and a pattern motion mechanism that, in operation, controls movement of a pattern relative to the sensing region. The pattern can be one of a pattern of excitation in the sensing region; a filtering pattern that receives light emanating from objects in the sensing region; and a sensing pattern with which the sensor interacts with objects in the sensing region.

In further specific implementations, the system can also include a fluidic structure with a channel that includes the sensing region and in which fluid carrying objects in the subset can flow in a longitudinal direction. The relative motion component can include both the fluidic motion mechanism and the channel motion mechanism, with the fluidic motion mechanism controlling flow of fluid in the longitudinal direction in the channel and the channel motion mechanism controlling movement of the channel in at least one lateral direction that is not parallel to the longitudinal direction. Also, the relative motion component can include a fluidic device that, in operation, drives the fluid through the channel in the longitudinal direction, causing objects in the subset to have respective longitudinal relative motion within the sensing region; channel wall parts of the fluidic structure can have inner surfaces bounding the sensing region and having shapes that cause the nonuniform relative motion and/or the relative motion component can include a displacement component that, in operation, causes time-varying relative displacement of objects within the sensing region, the displacement being in lateral directions not parallel to the longitudinal direction and causing the nonuniform relative motion.

In further specific implementations, the system can also include a movable support structure that can support objects. The relative motion component can include the support motion mechanism, which can include a scanner device that, in operation controls scanning movement of the movable support structure in at least one scanning direction and/or a rotary device that, in operation, controls rotating movement of the movable support structure.

In further specific implementations, the sensor can be movable. The relative motion component can include the sensor motion mechanism, which can include a scanner device that, in operation controls scanning movement of the movable support structure in at least one scanning direction and/or a rotary device that, in operation, controls rotating movement of the sensor.

In further specific implementations, the system can include a support structure capable of supporting objects and the relative motion component can be capable of moving one or both of the support structure so that an object supported on the support structure has respective relative motion within the sensing region. The system can also include control circuitry that provides control signals to cause the nonuniform relative motion, and the relative motion component can include a support motion mechanism and/or a sensor motion mechanism. The support motion mechanism can, in operation, control movement of the support structure, with the control circuitry providing control signals to the support motion mechanism causing the nonuniform relative motion. The sensor motion mechanism can, in operation, control movement of the sensor, with the control circuitry providing control signals to the sensor motion mechanism causing the nonuniform relative motion.

In further specific implementations, the system can include a processing component that, in response to sensing results, performs operations to obtain data indicating information resulting from the nonuniform relative motion within the sensing region. An encoder/sensor device can include the system, and can also include circuitry that provides control signals in response to which the relative motion component causes the nonuniform relative motion; the circuitry can also receive signals that indicate the sensing component's sensing results. The circuitry can include a processor that provides the control signals and that, in response to the sensing results, performs operations to obtain data indicating information resulting from the nonuniform relative motion within the sensing region.

Some of the implementations described above in relation to FIGS. 1-14 are examples of a method of using sensors. The method includes operating a sensor to obtain sensing results from objects in a sensing region relative to the sensor. In operating the sensor, the method causes respective relative motion of each of a subset of the objects, and each object's relative motion includes respective relative motion within the sensing region. For at least one object in the subset, the respective relative motion within the sensing region is nonuniform, with the nonuniform motion including at least one of periodically varying relative motion, randomly varying relative motion, chirp-varying relative motion, and modulated relative motion that completes at least one modulation cycle within the sensing region.

In specific implementations, the act of operating the sensor can include operating it so that the sensing results indicate at least one waveform with time variation resulting from the nonuniform relative motion. The method can also use the sensing results to obtain data indicating information resulting from the nonuniform relative motion. Each object's relative motion can include respective relative motion into the sensing region and respective relative motion out of the sensing region. The act of causing respective relative motion can include varying speed of objects, varying direction of objects, controlling flow of fluid carrying objects, controlling movement of a channel through which objects are carried by fluid, controlling movement of a structure supporting objects, controlling movement of the sensor, and/or controlling pattern movement relative to the sensing region. The pattern whose movement is controlled can be a pattern of excitation as described above, a filtering pattern as described above, and/or a sensing pattern as described above.

In further specific implementations, the sensor can be an encoder/sensor and the act of causing respective relative motion can include controlling pattern movement. The act of controlling pattern movement can include controlling an excitation component of the sensor, where the excitation component provides the pattern of excitation; controlling a filtering component of the sensor, where the filtering component provides the filtering pattern; and/or controlling a sensing component of the sensor, where the sensing component provides the sensing pattern.

In further specific implementations, the act of causing relative motion can include causing fluid to carry objects in a channel that includes the sensing region; concurrently causing fluid to carry objects in a channel that includes the sensing region and causing time-varying motion of the channel; and/or causing relative motion modulation cycles between the sensor and a support structure that supports objects, with the nonuniform relative motion within the sensing region resulting from at least one relative motion modulation cycle. The channel can have wall parts with inner surfaces that bound the sensing region and that have shapes that cause the nonuniform relative motion. The act of concurrently causing fluid to carry objects and causing time-varying motion can include causing channel motion modulation cycles as objects are carried by fluid within the sensing region, and the nonuniform relative motion within the sensing region can result from at least one of the cycles. The act of causing relative motion modulation cycles can include causing carrier relative motion with uniform speed and direction between support structure and sensor and also causing modulating relative motion between sensor and support structure, where the modulating relative motion includes the relative motion modulation cycles. The carrier relative motion can be one of a scanning motion and a rotating motion. The uniform direction of the carrier relative motion can be in a scanning direction, and the modulating relative motion can be in the scanning direction and/or in a lateral direction that is not parallel to the scanning direction. Or the uniform direction of the carrier relative motion can be in a rotation direction of approximately constant curvature about an axis of rotation, and the modulating relative motion can be in the rotation direction, a radial direction toward or from the axis of rotation, and/or a lateral direction that is not parallel to a plane that includes the rotation direction and the radial direction.

Some of the implementations described above in relation to FIGS. 1-14 are examples of an encoder/sensor device that includes a sensing component, a relative motion component, and circuitry. The sensing component, in operation, obtains sensing results from objects in a sensing region relative to the sensing component. In operation, the relative motion component causes respective relative motion of each of a subset of the objects, and each object in the subset has respective relative motion within the sensing region. The relative motion component causes at least one object's relative motion within the sensing region to be nonuniform. The circuitry provides control signals in response to which the relative motion component causes the nonuniform relative motion; the circuitry also receives signals that indicate the sensing component's sensing results.

In specific implementations of encoder/sensor devices, the nonuniform relative motion within the sensing region can include at least one of periodically varying relative motion, randomly varying relative motion, chirp-varying relative motion, and modulated relative motion that completes at least one modulation cycle within the sensing region. The sensing results can include motion-encoded information resulting from the nonuniform relative motion. The circuitry can also include a processor as described above.

In further specific implementations, the encoder/sensor device can also include at least one of excitation circuitry as described above and filter circuitry as described above. The sensing component can include a photosensor and/or an impedance-based sensor.

In further specific implementations, the encoder/sensor device can include at least one of an excitation component as described above; a filter component as described above; and sensor circuitry that performs sensing by interacting with objects in the sensing region with a sensing pattern. The relative motion can cause the nonuniform relative motion between objects in the subset and the pattern of excitation; the filtering pattern; and/or the sensing pattern with which the sensor interacts with objects in the sensing region.

In further specific implementations, the relative motion component can include at least one of a fluidic motion mechanism as described above; a channel motion mechanism as described above; and a support motion mechanism as described above.

In further specific implementations, the device can also include a fluidic structure as described above. The relative motion component can include both the fluidic motion mechanism and the channel motion mechanism as described above.

In further specific implementations, the device can also include a movable support structure as described above. The relative motion component can include the support motion mechanism, which can include a scanner device as described above and/or a rotary device as described above.

In further specific implementations, the sensing component can include a movable sensor. The relative motion component can include the sensor motion mechanism, which can include a scanner device as described above and/or a rotary device as described above.

Some of the implementations described above in relation to FIGS. 1-14 are examples of an article of manufacture that includes a fluidic structure and a fluidic device. The fluidic structure includes channel walls bounding a channel through which, in operation, fluid carries objects in a longitudinal direction; the channel includes a set of one or more regions each of which, in operation, is a sensing region relative to a respective sensor, and each region's sensor is capable of obtaining sensing results from objects in the region. The fluidic device, in operation, drives fluid through the channel in the longitudinal direction and causes objects to have respective longitudinal relative motion within each region. The article also includes at least one of the following: Channel wall parts with inner surfaces that bound a shaped-wall region that is in the set, where the inner surfaces have shapes that cause the respective relative motion of objects within the shaped-wall region to be nonuniform; and a displacement component that, in operation, causes time-varying relative displacement of objects within a displacement region in the set, with the relative displacement being in lateral directions not parallel to the longitudinal direction and causing at least one object's relative motion within the displacement region to be nonuniform.

In specific implementations that include the channel wall parts, the inner surfaces can include a pair of facing inner surfaces with varying separation from each other and/or a pair of facing inner surfaces that have periodic shapes of equal period and are parallel to each other. The nonuniform relative motion can include periodically varying relative motion, randomly varying relative motion, and/or chirp-varying relative motion.

In specific implementations that include the displacement control component, the displacement control component can include a channel motion mechanism that, in operation, controls movement of a part of the channel that includes the displacement region. Or the displacement control component can include a wall motion device that, in response to control signals, causes motion of movable wall parts that bound the displacement region; in operation, control circuitry can provide control signals to the wall motion device. The nonuniform relative motion can include periodically varying relative motion, randomly varying relative motion, chirp-varying relative motion, and/or modulated relative motion that completes at least one modulation cycle within the displacement region.

In further specific implementations, the respective sensor of at least one of the shaped-wall region and the displacement region is an encoder/sensor that includes excitation circuitry as described above, filter circuitry as described above, and/or sensor circuitry that, in operation, provides sensing results that indicate one or more waveforms with time variation resulting both from the nonuniform relative motion and from encoding performed independently of the nonuniform relative motion. The article can, for example, be a flow cytometer.

Some of the implementations described above in relation to FIGS. 1-14 are examples of an article of manufacture that includes a support structure that, in use, supports objects; a sensor; a relative motion component; and control circuitry. The relative motion component, in response to control signals, moves one or both of the support structure and the sensor causing objects supported on the support structure to have respective relative motion within a sensing region relative to the sensor, which is capable of obtaining sensing results from objects in the sensing region. The relative motion component includes a support motion mechanism that, in operation, controls movement of the support structure and/or a sensor motion mechanism that, in operation, controls movement of the sensor. The control circuitry provides control signals in response to which the relative motion component causes at least one object's relative motion within the sensing region to be nonuniform.

In specific implementations, the nonuniform relative motion can include at least one of periodically varying relative motion, randomly varying relative motion, chirp-varying relative motion, and modulated relative motion that completes at least one modulation cycle within the sensing region. The relative motion component can include both the support motion mechanism and the sensor motion mechanism, and can cause the nonuniform relative motion by concurrently operating both. The support structure can be a slide on which objects are supported, a disk on which objects are supported, and/or a fluidic structure that contains objects.

In further specific implementations, the article includes a scanner device and/or a rotary device. The scanner device can include a first support component that supports the support structure, a second support component that supports the sensor, and the relative motion component; the control signals can include scan control signals and displacement control signals; and the relative motion component can respond to the scan control signals by causing scanning relative movement between the support structure and the sensor and to the displacement control signals by causing displacement relative movement between them. The rotary device can include a first support component that supports the support structure, a second support component that supports the sensor, and the relative motion component; the control signals can include rotation control signals and displacement control signals; and the relative motion component can respond to the rotation control signals by causing rotating relative movement between the support structure and the sensor and to the displacement control signals by causing displacement relative movement between them.

Exemplary implementations described above employ photosensors or impedance-based sensors with specific features, but a wide variety of sensors could be used to obtain sensing results indicating values of various parameters other than emanating light intensity, parameters that can have time variation that indicates information resulting from nonuniform relative motion of objects within sensing regions. Similarly, implementations described above involve sensing information resulting from nonuniform relative motion of objects in fluidic channels or relative to a sensor such as in scanning or rotation, but various other types of fluidic implementations or other implementations in which objects have nonuniform relative motion in various other ways could be sensed to obtain sensing results as in techniques described above.

Components of exemplary implementations as described above could have various shapes, dimensions, or other numerical or qualitative characteristics other than those illustrated and described above. Similarly, although the exemplary fluidic implementations generally involve sensing from a single fluidic channel, implementations could readily include multiple parallel channels, allowing parallel sensing and readout and larger scale sensing.

Some of the above exemplary implementations involve specific types of trigger detectors, encoder/sensors, relative motion components, control circuitry, processing circuitry, and so forth, but the invention could be implemented with a wide variety of other types of components. For example, some implementations use specific types of spatial modulation based on nonuniform relative motion caused by one or more specified motion control mechanism, motion device, or displacement component, but various other types of spatial modulation could be used. Also, some exemplary implementations use specific types of processing, such as digital signals obtained after converting sensed analog values. In general, however, the invention could be implemented with any suitable signal processing techniques, including any appropriate combination of analog and digital processing; photosensed quantities could be combined either in analog or digital form; either or both of two compared waveforms could be obtained in analog or digital form, and any combination of time scaling could be performed before comparison. Further, some exemplary implementations use discrete, large area photosensors or impedance-based sensors, but various ICs with photosensing arrays might be used.

Some of the above exemplary implementations involve specific types of emanating light, e.g. fluorescence, and specific types of excitation, filtering, and photosensing suitable to fluorescent light, but these are merely exemplary. The invention could be implemented in relation to various other types of emanating light with various other types of excitation, filtering, and photosensing in various other ranges of photon energies or with any other appropriate sensed stimuli.

The exemplary implementation in FIG. 5 employs a CPU, which could be a microprocessor or any other appropriate component. Furthermore, as noted above, operations could be performed digitally or with analog signals, and could be done either on the same IC as a photosensor array, on other components, or on a combination of the two, with any appropriate combination of software or hardware.

The above exemplary implementations generally involve use of encoder/sensors, relative motion components, control circuitry, processing circuitry, and so forth following particular operations, but different operations could be performed, the order of the operations could be modified, and additional operations could be added within the scope of the invention.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A system comprising:
 a sensor that, in operation, obtains sensing results from objects in a sensing region relative to the sensor; and
 a relative motion component comprising a channel motion mechanism that, in operation, controls movement of a channel that includes the sensing region and through which objects are carried by fluid, the relative motion component, in operation, causing respective relative motion of each object of a subset of the objects in the sensing region; the objects in the subset each having respective relative motion within the sensing region; the relative motion component causing at least one object's relative motion within the sensing region to be nonuniform, the nonuniform relative motion within the sensing region including at least one of:
 periodically varying relative motion;
 randomly varying relative motion;
 chirp-varying relative motion; and
 modulated relative motion that completes at least one modulation cycle within the sensing region.

2. The system of claim 1 in which at least one of:
 the sensing results include motion-encoded information resulting from the nonuniform relative motion;
 the sensing results include independently encoded information resulting from encoding performed by the sensor independently of the nonuniform relative motion; and
 the sensing results indicate at least one waveform with time variation resulting from the nonuniform relative motion.

3. The system of claim 1 in which the sensor includes at least one of:
 an excitation component that provides a pattern of excitation in the sensing region;
 a filter component that filters light emanating from objects in the sensing region with a filtering pattern; and
 a sensing component that performs sensing by interacting with objects in the sensing region with a sensing pattern; the sensing component including one or both of a photosensor and an impedance-based sensor;
 the nonuniform relative motion within the sensing region including nonuniform relative motion between objects in the subset and at least one of:
 the pattern of excitation;
 the filtering pattern; and
 the sensing pattern.

4. The system of claim 1 in which the relative motion component further includes at least one of:
 a motion-varying mechanism that, in operation, causes the nonuniform relative motion by varying one or both of speed and direction of objects' relative motion within the sensing region;
 a fluidic motion mechanism that, in operation, controls flow of fluid carrying objects within the sensing region;
 a support motion mechanism that, in operation, controls movement of a structure supporting objects;
 a sensor motion mechanism that, in operation, controls movement of the sensor; and
 a pattern motion mechanism that, in operation, controls movement of a pattern relative to the sensing region, the pattern being one of:
 a pattern of excitation in the sensing region;
 a filtering pattern that receives light emanating from objects in the sensing region; and
 a sensing pattern with which the sensor interacts with objects in the sensing region.

5. The system of claim 4, further comprising:
 a fluidic structure with the channel that includes the sensing region and in which fluid carrying objects in the subset can flow in a longitudinal direction, the fluidic motion mechanism controlling flow of fluid in the longitudinal direction in the channel and the channel motion mechanism controlling movement of the channel in at least one lateral direction that is not parallel to the longitudinal direction.

6. The system of claim 4, further comprising:
 a movable support structure that can support objects; and
 the relative motion component including the support motion mechanism; the support motion mechanism including at least one of:
 a scanner device that, in operation, controls scanning movement of the movable support structure in at least one scanning direction; and
 a rotary device that, in operation, controls rotating movement of the movable support structure.

7. The system of claim 4 in which the sensor is movable, the relative motion component including the sensor motion mechanism; the sensor motion mechanism including at least one of:
 a scanner device that, in operation, controls scanning movement of the sensor in at least one scanning direction; and
 a rotary device that, in operation, controls rotating movement of the sensor.

8. A system comprising:
 a sensor that, in operation, obtains sensing results from objects in a sensing region relative to the sensor;
 a relative motion component that, in operation, causes respective relative motion of each object of a subset of the objects; the objects in the subset each having respective relative motion within the sensing region; the relative motion component causing at least one object's relative motion within the sensing region to be nonuniform, the nonuniform relative motion within the sensing region including at least one of:
 periodically varying relative motion;
 randomly varying relative motion;
 chirp-varying relative motion; and
 modulated relative motion that completes at least one modulation cycle within the sensing region; and a fluidic structure with a channel that includes the sensing region and in which fluid carrying objects in the subset can flow in a longitudinal direction, wherein the relative motion component further includes:
a fluidic device that, in operation, drives the fluid through the channel in the longitudinal direction, causing objects in the subset to have respective longitudinal relative motion within the sensing region;
in which at least one of:
the fluidic structure further includes channel wall parts with inner surfaces that bound the sensing region, the inner surfaces having shapes that cause the nonuniform relative motion; and
the relative motion component further includes a displacement component that, in operation, causes time-varying relative displacement of objects within the sensing region, the relative displacement being in lateral directions that are not parallel to the longitudinal direction and causing the nonuniform relative motion.

9. The system of claim 1, further comprising:
a support structure capable of supporting objects; the relative motion component being capable of moving one or both of the support structure and the sensor so that an object supported on the support structure has respective relative motion within the sensing region; and
control circuitry that provides control signals to cause the nonuniform relative motion; the relative motion component including at least one of:
a support motion mechanism that, in operation, controls movement of the support structure; the control circuitry providing control signals to the support motion mechanism causing the nonuniform relative motion; and
a sensor motion mechanism that, in operation, controls movement of the sensor; the control circuitry providing control signals to the sensor motion mechanism causing the nonuniform relative motion.

10. An encoder/sensor device comprising the system of claim 1; the device further comprising:
circuitry that provides control signals in response to which the relative motion component causes the nonuniform relative motion and that receives signals that indicate the sensing component's sensing results.

11. The device of claim 10 in which the circuitry includes:
a processor that provides the control signals and that, in response to the sensing results, performs operations to obtain data indicating information resulting from the nonuniform relative motion within the sensing region.

12. A method of using sensors, the method comprising:
operating a sensor to obtain sensing results from objects in a sensing region relative to the sensor; the act of operating the sensor comprising:
causing respective relative motion of each object of a subset of the objects, each object's relative motion including respective relative motion within the sensing region; for at least one object in the subset, the respective relative motion within the sensing region being nonuniform and between at least two sensing subregions of the sensing region, the nonuniform relative motion within the sensing region including at least one of:
periodically varying relative motion;
randomly varying relative motion;
chirp-varying relative motion; and
modulated relative motion that completes at least one modulation cycle within the sensing region.

13. The method of claim 12 in which the act of causing respective relative motion includes at least one of:
varying speed of objects;
varying direction of objects;
controlling flow of fluid carrying objects;
controlling movement of a channel through which objects are carried by fluid;
controlling movement of a structure supporting objects;
controlling movement of the sensor; and
controlling pattern movement relative to the sensing region of at least one of:
a pattern of excitation in the sensing region;
a filtering pattern that receives light emanating from objects in the sensing region; and
a sensing pattern with which the sensor interacts with objects in the sensing region.

14. The method of claim 12 in which the act of causing respective relative motion includes at least one of:
causing fluid to carry objects in a channel that includes the sensing region, the channel having wall parts with inner surfaces that bound the sensing region, the inner surfaces having shapes that cause the nonuniform relative motion;
concurrently causing fluid to carry objects in a channel that includes the sensing region and causing time-varying motion of the channel; the act of concurrently causing fluid to carry objects in a channel and causing time-varying motion of the channel including:
causing channel motion modulation cycles as objects are carried by fluid within the sensing region, the nonuniform relative motion within the sensing region resulting from at least one of the channel motion modulation cycles; and
causing relative motion modulation cycles between the sensor and a support structure that supports objects, the nonuniform relative motion within the sensing region resulting from at least one of the relative motion modulation cycles; the act of causing relative motion modulation cycles comprising:
causing carrier relative motion with uniform speed and direction between the support structure and the sensor; and
causing modulating relative motion between the sensor and the support structure, the modulating relative motion including the relative motion modulation cycles.

15. The method of claim 14 in which the carrier relative motion is one of a scanning motion and a rotating motion.

16. The method of claim 14 in which the uniform direction of the carrier relative motion is in a scanning direction, the modulating relative motion being in at least one of:
the scanning direction; and
a lateral direction that is not parallel to the scanning direction.

17. The method of claim 14 in which the uniform direction of the carrier relative motion is in a rotation direction of approximately constant curvature about an axis of rotation, the modulating relative motion being in at least one of:
the rotation direction;
a radial direction toward or from the axis of rotation; and
a lateral direction that is not parallel to a plane that includes the rotation direction and the radial direction.

18. An article of manufacture comprising:
a fluidic structure that includes channel walls bounding a channel through which, in operation, fluid carries objects in a longitudinal direction; the channel including a set of one or more regions each of which, in operation, is a sensing region relative to a respective sensor, each region's sensor being capable of obtaining sensing results from objects in the region; and a fluidic device that, in operation, drives fluid through the channel in the longitudinal direction and that causes objects to have respective longitudinal relative motion within each region;

the article further comprising at least one of:

channel wall parts with inner surfaces that bound a shaped-wall region that is in the set, the inner surfaces having shapes that cause the respective relative motion of objects within the shaped-wall region to be nonuniform; and a displacement component that, in operation, causes time-varying relative displacement of objects within a displacement region in the set, the relative displacement being in lateral directions that are not parallel to the longitudinal direction and causing at least one object's relative motion within the displacement region to be nonuniform.

19. The article of claim 18 in which the article includes the channel wall parts; the inner surfaces including at least one of:

a pair of facing inner surfaces that have varying separation from each other;

a pair of facing inner surfaces that have periodic shapes of equal period and that are substantially parallel to each other; and a pair of facing inner surfaces that have random shapes and that are substantially parallel to each other.

20. The article of claim 18 in which the article is a flow cytometer.

21. An article of manufacture comprising:

a support structure that, in use, support objects;

a sensor;

a relative motion component that, in response to control signals, moves one or both of the support structure and the sensor causing objects supported on the support structure to have respective relative motion within a sensing region relative to the sensor, the sensor being capable of obtaining sensing results from objects in the sensing region; the relative motion component including at least one of:

a support motion mechanism that, in operation, controls movement of the support structure; and a sensor motion mechanism that, in operation, controls movement of the sensor; and control circuitry that provides control signals in response to which the relative motion component causes at least one object's relative motion within the sensing region to be nonuniform and between at least two sensing subregions of the sensing region.

22. The article of claim 21 in which the support structure is at least one of:

a slide on which objects are supported;

a disk on which objects are supported; and a fluidic structure that contains objects.

23. The article of claim 21, further comprising at least one of:

a scanner device; the scanner device including:

a first support component that supports the support structure;

a second support component that supports the sensor; and the relative motion component;

the control signals including:

scan control signals in response to which the relative motion component causes scanning relative motion between the support structure and the sensor; and displacement control signals in response to which the relative motion component causes displacement relative motion between the support structure and the sensor; and a rotary device; the rotary device including:

a first support component that supports the support structure;

a second support component that supports the sensor; and the relative motion component;

the control signals including:

rotation control signals in response to which the relative motion component causes rotating relative motion between the support structure and the sensor; and displacement control signals in response to which the relative motion component causes displacement relative motion between the support structure and the sensor.

\* \* \* \* \*